(12) United States Patent
Nelson et al.

(10) Patent No.: US 12,138,843 B2
(45) Date of Patent: Nov. 12, 2024

(54) EXTRUDED HYDROGEL TUBES AND COAXIAL FIBERS AND APPLICATIONS THEREOF

(71) Applicant: UNIVERSITY OF WASHINGTON, Seattle, WA (US)

(72) Inventors: Alshakim Nelson, Seattle, WA (US); Siyami Millik, Seattle, WA (US); Patrick Smith, Seattle, WA (US); Dylan Karis, Seattle, WA (US); Ashleigh Theberge, Seattle, WA (US); Ashley Dostie, Seattle, WA (US)

(73) Assignee: University of Washington, Seattle, WA (US)

( * ) Notice: Subject to any disclaimer, the term of this patent is extended or adjusted under 35 U.S.C. 154(b) by 757 days.

(21) Appl. No.: 17/251,735

(22) PCT Filed: Jun. 13, 2019

(86) PCT No.: PCT/IB2019/054930
§ 371 (c)(1),
(2) Date: Dec. 11, 2020

(87) PCT Pub. No.: WO2019/239359
PCT Pub. Date: Dec. 19, 2019

(65) Prior Publication Data
US 2021/0114276 A1    Apr. 22, 2021

Related U.S. Application Data

(60) Provisional application No. 62/684,540, filed on Jun. 13, 2018, provisional application No. 62/843,195, filed on May 3, 2019.

(51) Int. Cl.
*B29C 48/09* (2019.01)
*B29C 35/08* (2006.01)
(Continued)

(52) U.S. Cl.
CPC .......... *B29C 48/09* (2019.02); *B29C 35/0805* (2013.01); *B29C 48/05* (2019.02);
(Continued)

(58) Field of Classification Search
None
See application file for complete search history.

(56) References Cited

U.S. PATENT DOCUMENTS 5,225,120 A    7/1993 Graiver et al.
5,614,276 A    3/1997 Petsetakis
(Continued)

FOREIGN PATENT DOCUMENTS

CN    105963050    9/2016
CN    106178130    12/2016
(Continued)

OTHER PUBLICATIONS

"A versatile method for combining different biopolymers in a core/shell fashion by 3D plotting to achieve mechanically robust constructs" (Akkineni et al. Biofabrication Aug. 2016 (Oct. 7, 2016)). (Year: 2016).*
(Continued)

*Primary Examiner* — Robert J Grun
(74) *Attorney, Agent, or Firm* — Kilpatrick Townsend & Stockton LLP

(57) ABSTRACT

Methods of fabricating a hydrogel tube, and related systems, employ extrusion of a cross-linkable hydrogel solution from an annular outer nozzle of a nozzle assembly to form a cross-linkable hydrogel tube. The cross-linkable hydrogel tube is cured to form a cross-linked hydrogel tube. A second hydrogel solution can be coextruded via the axial inner nozzle to form an inner hydrogel filament coaxially positioned within the cross-linkable hydrogel tube. The cross-linked hydrogel tube can be functionalized with collagen to
(Continued)

enable cell adhesion, and cells can be cultured on the luminal surfaces of these tubes to yield tubular endothelial layers. A 3D printed coaxial nozzle can be used to fabricate biofunctional tubular conduits that can be utilized for engineering in vitro models of tubular biological structures.

12 Claims, 22 Drawing Sheets

(51) Int. Cl.
    *B29C 48/05*     (2019.01)
    *B29C 48/16*     (2019.01)
    *B29C 48/30*     (2019.01)
    *B29C 48/475*     (2019.01)
    *B29C 48/88*     (2019.01)
    *C12M 1/12*     (2006.01)
    *B29K 77/00*     (2006.01)
    *B29K 105/00*     (2006.01)
    *B29K 105/24*     (2006.01)

(52) U.S. Cl.
    CPC .............. *B29C 48/16* (2019.02); *B29C 48/30* (2019.02); *B29C 48/475* (2019.02); *B29C 48/912* (2019.02); *C12M 23/06* (2013.01); *C12M 25/14* (2013.01); *B29C 2035/0827* (2013.01); *B29K 2077/00* (2013.01); *B29K 2105/0061* (2013.01); *B29K 2105/243* (2013.01); *B29K 2105/258* (2013.01)

(56) References Cited

U.S. PATENT DOCUMENTS

| | | | |
|---|---|---|---|
| 6,368,356 | B1 | 4/2002 | Zhong et al. |
| 2008/0072647 | A1 | 3/2008 | Okui et al. |
| 2015/0084232 | A1 | 3/2015 | Rutz et al. |
| 2016/0177002 | A1 | 6/2016 | Palchik et al. |
| 2017/0056551 | A1 | 3/2017 | Dubey et al. |
| 2017/0267883 | A1 | 9/2017 | Engler et al. |
| 2017/0327813 | A1 | 11/2017 | Cattolico et al. |

FOREIGN PATENT DOCUMENTS

| | | |
|---|---|---|
| JP | 2017077245 | 4/2017 |
| WO | 2015048355 | 4/2015 |
| WO | 2019239359 | 12/2019 |

OTHER PUBLICATIONS

Atala et al., "The Potential Role of Tissue-Engineered Urethral Substitution: Clinical and Preclinical Studies", Journal of Tissue Engineering and Regenerative Medicine, vol. 11, No. 1, Jan. 2017, pp. 3-19.
Atlan et al., "A New Synthetic Model for Microvascular Anastomosis Training? A Randomized Comparative Study Between Silicone and Polyvinyl Alcohol Gelatin Tubes", Journal of Surgical Education, vol. 75, No. 1, Jan.-Feb. 2018, pp. 182-187.
Basu et al., "Catalytically Initiated Gel-in-Gel Printing of Composite Hydrogels", ACS Applied Materials & Interfaces, Nov. 1, 2017, pp. 40898-40904.
Battiston et al., "Literature Review and Personal Clinical Experience Comparing Biological and Synthetic Conduits for Sensory Nerve Repair", Microsurgery, vol. 25, No. 4, Jan. 2005, pp. 258-267.
Caliari et al., "A Practical Guide to Hydrogels for Cell Culture", Nature Methods, vol. 13, No. 5, Apr. 2016, pp. 405-414.
Carvalho et al., "Tunable Enzymatically Cross-Linked Silk Fibroin Tubular Conduits for Guided Tissue Regeneration", Advanced Healthcare Materials, vol. 7, No. 17, Sep. 2018, 15 pages.
Celikkin et al., "3D Printing of Thermoresponsive Polyisocyanide (PIC) Hydrogels as Bioink and Fugitive Material for Tissue Engineering", Polymers, vol. 10, No. 5, May 2018, pp. 1-11.
Chaouat et al., "A Novel Cross-linked Poly(vinyl alcohol) (PVA) for Vascular Grafts", Advanced Functional Materials, vol. 18, No. 19, Oct. 6, 2008, pp. 2855-2861.
Ci et al., "Amino-Functionalized Poloxamer 407 with Both Mucoadhesive and Thermosensitive Properties: Preparation, Characterization and Application in a Vaginal Drug Delivery System", Acta Pharmaceutica Sinica B, vol. 7, No. 5, Mar. 2017, pp. 593-602.
Cochis et al., "3D Printing of Thermo-Responsive Methylcellulose Hydrogels for Cell-Sheet Engineering", Material, vol. 11, No. 4, Apr. 10, 2018, pp. 1-14.
Colosi et al., "Microfluidic Bioprinting of Heterogeneous 3D Tissue Constructs Using Low-Viscosity", Advanced Materials, vol. 28, No. 4, Jan. 27, 2016, pp. 677-684.
Costantini et al., "Co-Axial Wet-Spinning In 3D Bioprinting: State of The Art And Future Perspective of Microfluidic Integration", Biofabrication, vol. 11, No. 1, Nov. 9, 2018, pp. 1-14.
De Filippo et al., "Urethral Replacement Using Cell Seeded Tubularized Collagen Matrices", Journal of Urology, vol. 168, No. 4, Supplement 2, Oct. 2002, pp. 1789-1793.
Duchi et al., "Handheld Co-Axial Bioprinting: Application to in Situ Surgical Cartilage Repair", Scientific Reports, vol. 7, No. 1, Jul. 19, 2017, 12 pages.
Elomaa et al., "Additive Manufacturing of Vascular Grafts and Vascularized Tissue Constructs", Tissue Engineering: Part B, vol. 23, No. 5, 2017, pp. 436-450.
Fan et al., "Bio-Printing Cell-Laden Matrigel-Agarose Constructs", Journal of Biomaterials Applications, vol. 31, No. 15, Nov. 2016, pp. 684-692.
Gao et al., "Coaxial Nozzle-Assisted 3D Bioprinting With Built-In Microchannels For Nutrients Delivery", Biomaterials, vol. 61, 2015, pp. 203-215.
Gao et al., "Tissue Engineered Bio-Blood-Vessels Constructed Using a Tissue-Specific Bioink and 3D Coaxial Cell Printing Technique: A Novel Therapy for Ischemic Disease", Advanced Functional Materials, vol. 27, No. 33, Jul. 19, 2017, 12 pages.
Gioffredia et al., "Pluronic F127 Hydrogel Characterization and Biofabrication in Cellularized Constructs for Tissue Engineering Applications", Procedia CIRP, vol. 49, Dec. 2016, pp. 125-132.
Hoffman, "Hydrogels for Biomedical Applications", Advanced Drug Delivery Reviews, vol. 64, Dec. 2012, pp. 18-23.
Homan et al., "Bioprinting of 3D Convoluted Renal Proximal Tubules on Perfusable Chips", Scientific Reports, vol. 6, No. 34845, Oct. 11, 2016, pp. 1-13.
Jia et al., "Direct 3D Bioprinting of Perfusable Vascular Constructs Using a Blend Bioink", Biomaterials, vol. 106, 2016, pp. 58-68.
Jin et al., "Printability Study of Hydrogel Solution Extrusion in Nanoclay Yield-Stress Bath During Printing-then-Gelation Biofabrication", Materials Science and Engineering C, vol. 80, 2017, pp. 313-325.
Johnson et al., "3D Printed Anatomical Nerve Regeneration Pathways", Advanced Functional Materials, vol. 25, No. 39, Oct. 21, 2015, pp. 6205-6217.
Kolesky et al., "3D Bioprinting of Vascularized, Heterogeneous Cell-Laden Tissue Constructs", Advanced Materials, vol. 26, No. 19, May 21, 2014, pp. 3124-3130.
Kolesky et al., "Three-Dimensional Bioprinting of Thick Vascularized Tissues", Proceedings of the National Academy of Sciences of the United States of America, vol. 113, No. 12, Mar. 22, 2016, pp. 3179-3184.
Li et al., "Generation, Endothelialization, and Microsurgical Suture Anastomosis of Strong 1-mm-Diameter Collagen Tubes", Tissue Engineering Part A, vol. 23, No. 7-8, Apr. 2017, pp. 335-344.
Li, "Study of Hydrogels for 3D Printing of Constructs With Strong Interfacial Bonding", Mechanical Engineering Doctoral Thesis, Nanyang Technological University, 2018, 172 pages.
Liu et al., "3D Printing of Living Responsive Materials and Devices", Advanced Materials, vol. 30, No. 4, Jan. 25, 2018, pp. 1-9.
Lucas et al., "The Plant Vascular System: Evolution, Development and Functions", Journal of Integrative Plant Biology, vol. 55, No. 4, Apr. 2013, pp. 294-388.

(56) References Cited

OTHER PUBLICATIONS

Ma et al., "Fabrication of 3D Tubular Hydrogel Materials through On-Site Surface Free Radical Polymerization", Chemistry of Materials, vol. 30, No. 19, Sep. 2018, pp. 6756-6768.

Macchiarini et al., "Clinical Transplantation of a Tissue-Engineered Airway", The Lancet, vol. 372, No. 9655, Dec. 13, 2008, pp. 2023-2030.

Malda et al., "25th Anniversary Article: Engineering Hydrogels for Biofabrication", Advanced Materials, vol. 25, No. 36, Sep. 25, 2013, pp. 5011-5028.

Melchiorri et al., "In Vitro Endothelialization of Biodegradable Vascular Grafts Via Endothelial Progenitor Cell Seeding and Maturation in a Tubular Perfusion System Bioreactor", Tissue Engineering Part C: Methods, vol. 22, No. 7, Jul. 2016, pp. 663-670.

Merceron et al., "Hydrogels for 3D Bioprinting Applications", Chapter 14, Essentials of 3D Biofabrication and Translation, Dec. 2015, pp. 249-270.

Mistry et al., "Bioprinting Using Mechanically Robust Core-Shell Cell-Laden Hydrogel Strands", Macromolecular Bioscience, vol. 17, No. 6, Jun. 2017, 8 pages.

Monahan-Earley et al., "Evolutionary Origins of the Blood Vascular System and Endothelium", Journal of Thrombosis and Haemostasis, vol. 11, Suppl 1, Jun. 2013, pp. 46-66.

Müller et al., "Nanostructured Pluronic Hydrogels as Bioinks for 3D Bioprinting", Biofabrication, vol. 7, No. 3, Aug. 11, 2015, pp. 1-17.

Murphy et al., "3D Bioprinting of Tissues and Organs", Nature Biotechnology, vol. 32, No. 8, Aug. 5, 2014, pp. 773-785.

O'Brien, "Biomaterials & Scaffolds for Tissue Engineering", Materials Today, vol. 14, No. 3, Mar. 2011, pp. 88-95.

O'Bryan et al., "Self-Assembled Micro-Organogels for 3D Printing Silicone Structures", Science Advances, vol. 3, No. 5, May 10, 2017, 8 pages.

Ouyang et al., "A Generalizable Strategy for the 3D Bioprinting of Hydrogels from Nonviscous Photo-Crosslinkable Inks", Advanced Materials, vol. 29, No. 8, Feb. 2017, 7 pages.

Ouyang et al., "Facile Biofabrication of Heterogeneous Multilayer Tubular Hydrogels by Fast Diffusion-Induced Gelation", ACS Applied Materials & Interfaces, vol. 10, No. 15, Mar. 2018, pp. 12424-12430.

Paxton et al., "Proposal to Assess Printability of Bioinks for Extrusion-Based Bioprinting and Evaluation of Rheological Properties Governing Bioprintability", Biofabrication, vol. 9, No. 4, Nov. 14, 2017, pp. 1-18.

PCT/IB2019/054930, "International Preliminary Report on Patentability", Dec. 24, 2020, 11 pages.

PCT/IB2019/054930, "International Search Report and Written Opinion", Jan. 29, 2020, 15 pages.

PCT/IB2019/054930, "Invitation to Pay Additional Fees and, Where Applicable, Protest Fee", Dec. 2, 2019, 3 pages.

Pi et al., "Digitally Tunable Microfluidic Bioprinting of Multilayered Cannular Tissues", Advanced Materials, vol. 30, No. 43, Oct. 2018, 18 pages.

Place et al., "Complexity in Biomaterials for Tissue Engineering", Nature Materials, vol. 8, No. 6, Jun. 2009, pp. 457-470.

Raphael et al., "3D Cell Bioprinting of Self-Assembling Peptide-Based Hydrogels", Materials Letters, vol. 190, Mar. 1, 2017, pp. 103-106.

Ratcliffe, "Tissue Engineering of Vascular Grafts", Matrix Biology, vol. 19, No. 4, Aug. 2000, pp. 353-357.

Raya-Rivera et al., "Tissue-Engineered Autologous Urethras for Patients Who Need Reconstruction: An Observational Study", The Lancet, vol. 377, No. 9772, Apr. 2, 2011, pp. 1175-1182.

Slaughter et al., "Hydrogels in Regenerative Medicine", Advanced Materials, vol. 21, Sep. 4, 2009, pp. 3307-3329.

Smith et al., "Chemical Modification and Printability of Shear-Thinning Hydrogel Inks for Direct-Write 3D Printing", Polymer, vol. 152, 2018, pp. 42-50.

Song et al., "Complex 3D-Printed Microchannels within Cell-Degradable Hydrogels", Advanced Functional Materials, vol. 28, Jun. 7, 2018, 10 pages.

Stichler et al., "Thiol-ene Cross-Linkable Hydrogels as Bioinks for Biofabrication", Macromolecular Symposia, vol. 372, No. 1, Apr. 19, 2017, pp. 102-107.

Suntornnond et al., "A Highly Printable and Biocompatible Hydrogel Composite for Direct Printing of Soft and Perfusable Vasculature-Like Structures", Scientific Reports, vol. 7, No. 1, Dec. 4, 2017, pp. 1-11.

Syedain et al., "A Completely Biological "off-the-shelf" Arteriovenous Graft That Recellularizes in Baboons", Science Translational Medicine, vol. 9, No. 414, Nov. 1, 2017, 11 pages.

Weinberg et al., "A Blood Vessel Model Constructed From Collagen and Cultured Vascular Cells", Science, vol. 231, No. 4736, Jan. 24, 1986, pp. 397-400.

Wenger et al., "3D Printing Applied to Tissue Engineered Vascular Grafts", Applied Sciences, vol. 8, No. 12, Dec. 2018, pp. 1-16.

Wu et al., "Omnidirectional Printing of 3D Microvascular Networks", Advanced Materials, vol. 23, No. 24, Jun. 24, 2011, pp. H178-H183.

Yu et al., "A Hybrid Bioprinting Approach for Scale-Up Tissue Fabrication", Journal of Manufacturing Science and Engineering, vol. 136, No. 6, Dec. 2014, 9 pages.

Zhang et al., "Characterization of Printable Cellular Micro-Fluidic Channels for Tissue Engineering", Biofabrication, vol. 5, No. 2, 2013, pp. 1-11.

Zhang et al., "In Vitro Study of Directly Bioprinted Perfusable Vasculature Conduits", Biomaterials Science, vol. 3, No. 1, Jan. 1, 2015, pp. 134-143.

Zhou et al., "Spider-Inspired Multicomponent 3D Printing Technique for Next-Generation Complex Biofabrication", ACS Applied Bio Materials, vol. 1, Jul. 12, 2018, pp. 502-510.

* cited by examiner

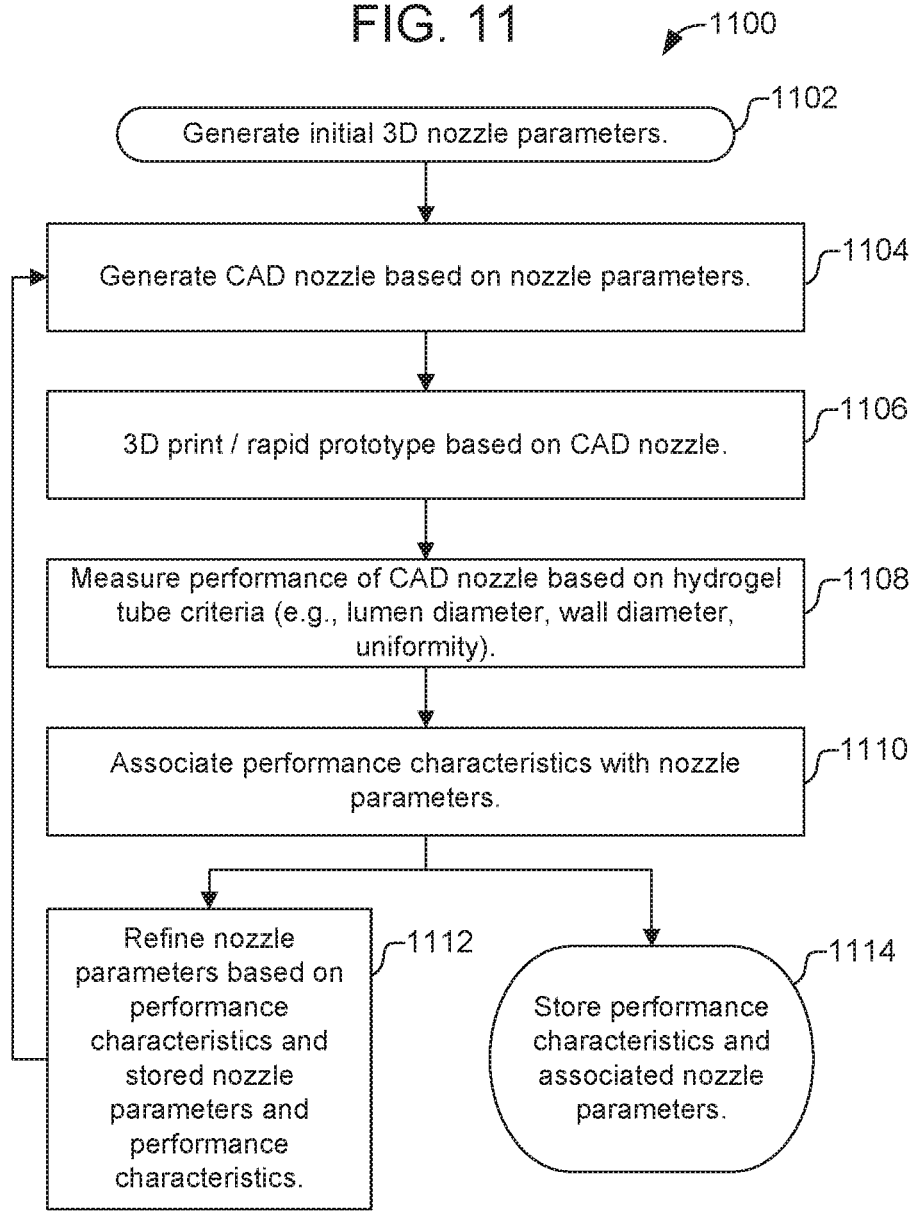

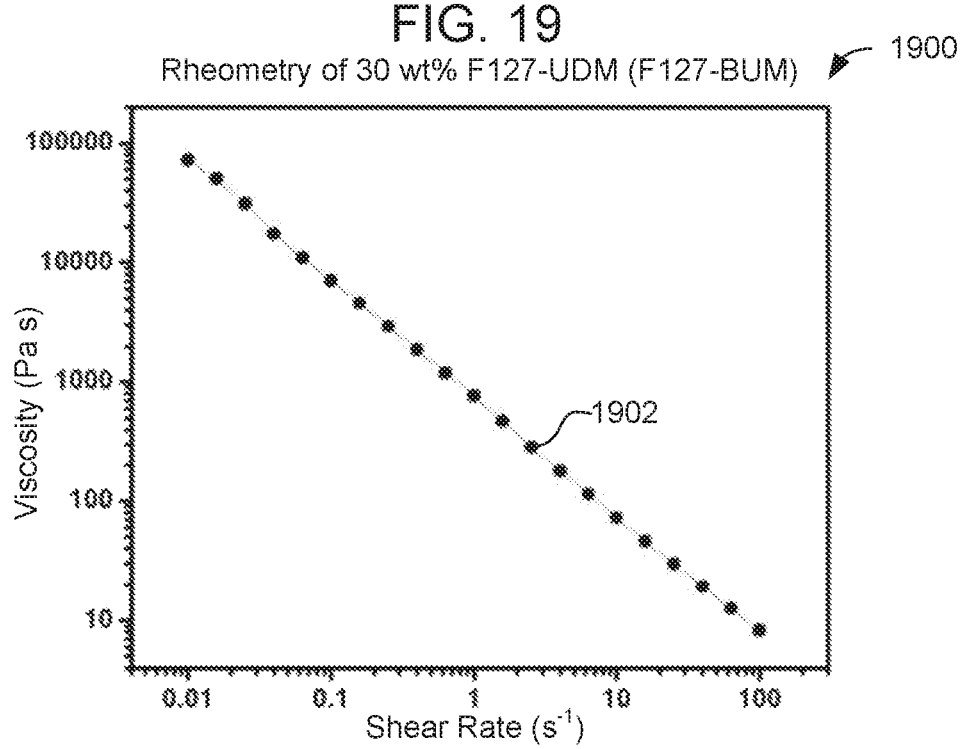

2300a

2300b

2300c

EXTRUDED HYDROGEL TUBES AND COAXIAL FIBERS AND APPLICATIONS THEREOF

CROSS-REFERENCES TO RELATED APPLICATIONS

This application is a U.S. 371 Application of International Application No. PCT/IB2019/054930, filed Jun. 13, 2019, which claims the benefit of U.S. Provisional Application No. 62/684,540, filed Jun. 13, 2018, and U.S. Provisional Application No. 62/843,195, filed May 3, 2019, the entire contents of which are hereby incorporated by reference for all purposes.

BACKGROUND

Tubular structures are abundant in nature where they function broadly as conduits for the bulk transport of fluids. Examples include the airways and blood vessels of vertebrates, and the xylems and phloems of vascular plants. Fabrication of perfusable structures using biofunctional materials and compatible manufacturing processes is of great interest in the areas of bioengineering (e.g., for in vitro assays) and regenerative medicine. While tubes are geometrically simple, their fabrication from soft materials is an existing challenge in the field. Common strategies involve casting or rolling a synthetic or natural polymeric material around a mandrel, wherein the diameter of the mandrel determines the tube's luminal diameter. Mandrel-based approaches can yield tubes with properties comparable to those of human blood vessels, however, the utility of these approaches is limited when it comes to the fabrication of tubes with small luminal diameters (<0.5 mm) and arbitrary lengths (>15 cm). To that end, improved methods for fabricating polymeric tubes and associated biomimetics are needed.

BRIEF SUMMARY

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings and each claim.

In some embodiments, methods of preparing a hydrogel tube include, with a nozzle assembly having an annular outer nozzle, extruding a cross-linkable hydrogel solution via the annular outer nozzle to form an outer cross-linkable hydrogel tube and curing the outer cross-linkable hydrogel tube to form a cross-linked hydrogel tube. According to some embodiments, these methods can be performed in conjunction with a bell-shaped nozzle producing a hollow hydrogel tube, or can be conducted with a coaxial nozzle producing a coaxial hydrogel filament, whereby an inner hydrogel filament supports the cross-linkable hydrogel tube prior to curing.

In some embodiments, additional methods for preparing of a hydrogel tube include cooling a first hydrogel solution to a sol state, loading the first hydrogel solution into a first pneumatic syringe barrel, cooling a second hydrogel solution to a sol state, loading the second hydrogel solution into a second pneumatic syringe barrel, warming both hydrogel solutions to a gel state, and subsequently coextruding the hydrogel solutions through a coaxial nozzle. The extrusion can be conducted by, e.g., attaching the first pneumatic syringe barrel to a first inlet of a concentric nozzle assembly, attaching the second pneumatic syringe barrel to a second inlet of the concentric nozzle assembly, and coextruding the first hydrogel solution from an annular nozzle outlet and the second hydrogel solution from an axial nozzle outlet to form a coaxial hydrogel filament. The coaxial hydrogel filament, which includes an outer cross-linkable hydrogel tube around an inner support hydrogel filament, can be processed into a hollow and durable hydrogel tube by curing the outer cross-linkable hydrogel tube to form a durable outer hydrogel tube, and removing the inner support hydrogel filament from the durable outer hydrogel tube.

In some embodiments, methods for preparing a hydrogel tube with an endothelial layer of endothelial include extruding a first cross-linkable hydrogel solution to form a cross-linkable hydrogel tube, e.g. according to any of the methods described herein, and subsequently curing the cross-linkable hydrogel tube to form a durable hydrogel tube, and subsequently seeding endothelial cells on a luminal surface of the durable hydrogel tube. According to some embodiments, suitable methods can further include impregnating the cross-linkable hydrogel solution with collagen by, e.g., including a collagen suspension in the cross-linkable hydrogel solution prior to suspension and/or cross-linking collagen to the luminal surface of the durable hydrogel tube.

In some embodiments, a hydrogel construct includes a cured hydrogel tube including a cross-linked hydrogel tube defining a luminal surface having collagen embedded therein or forming a layer thereon, and endothelial cells seeded on the luminal surface of the cured hydrogel tube. Cured hydrogel tubes can be formed according to any of the methods described herein.

In some embodiments, a nozzle assembly, e.g. for extruding hydrogel constructs, includes a nozzle body, first and second fluid inlets in the nozzle body, and a coaxial set of nozzle outlets at an apical end of the nozzle body. These nozzle outlets can include an inner nozzle outlet at an apical end of the nozzle body fluidly connected with the first fluid inlet and aligned with an axis of extrusion, and an outer nozzle outlet at the apical end of the nozzle body fluidly connected with the second fluid inlet and circumscribing the inner nozzle outlet. The outer nozzle outlet may be angled toward the axis of extrusion such that, in use, fluid extruded from the outer nozzle outlet would contact fluid extruded from the inner nozzle outlet.

BRIEF DESCRIPTION OF THE DRAWINGS

FIG. 11 illustrates an example process for iteratively developing 3D-printable nozzle geometries.

FIG. 19 is a first graph illustrating the rheological properties of F127-UDM, specifically a relationship between viscosity and shear rate demonstrating shear thinning.

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Various embodiments disclosed herein generally directed to the fabrication of tubular structures of flexible hydrogels. For example, according to some embodiments, tubular hydrogel structures can be fabricated by material extrusion through dies with annular orifices. Standalone tubular structures can be used as, e.g., vascular grafts, nerve guidance conduits, grafts for urethroplasty, and tracheal grafts, among other applications. More complex, perfusable, cell-laden constructs (e.g., containing endothelial cells) which utilize tubes as a basic structural motif can be used to recapitulate tissue or organ function. According to some specific embodiments, tubular hydrogel structures can be formed to encapsulate a perfusable volume suitable for, e.g., use as a small-scale bioreactor for the generation of useful biological products, for fermentation, or other uses. Disclosed herein are systems and processes for fabricating coaxial fibers and hollow tubes formed of hydrogel compositions. According to several embodiments of the present invention, hydrogel fibers and tubes can be extruded or printed by way of custom 3D printed nozzles, using hydrogel "inks" which can be modified to tune the physical and chemical properties of the corresponding hydrogel.

While other nozzle designs have been reported,[1-3] it is believed that none of these to-date have been entirely 3D printed. Coaxial nozzle designs with sub-millimeter orifices can be printed using stereolithographic 3D printers, which cannot be achieved otherwise. Moreover, the availability of hydrogels suitable for extrusion-based methods or printing have been limited primarily to calcium alginate-based hydrogels. The hydrogels are stimuli-responsive in several ways. First, the hydrogels are temperature responsive which facilitates the incorporation of additives. Second, the hydrogels are shear-thinning, which enables direct extrusion from a nozzle without additional additives. This second feature is in contrast to calcium alginate which requires the combination of sodium alginate and calcium to induce gelation. And third, the hydrogel formulation covalently cross-links in the presence of UV light to afford a mechanically robust structure. The coaxial fibers and hollow tubes generated from the approach described herein can be utilized for a broad range of applications including fluidic devices, artificial tissue, and vascular implants.

Preparing Durable Hydrogel Tubes Using Concentric Nozzle Methods

Figure 1:
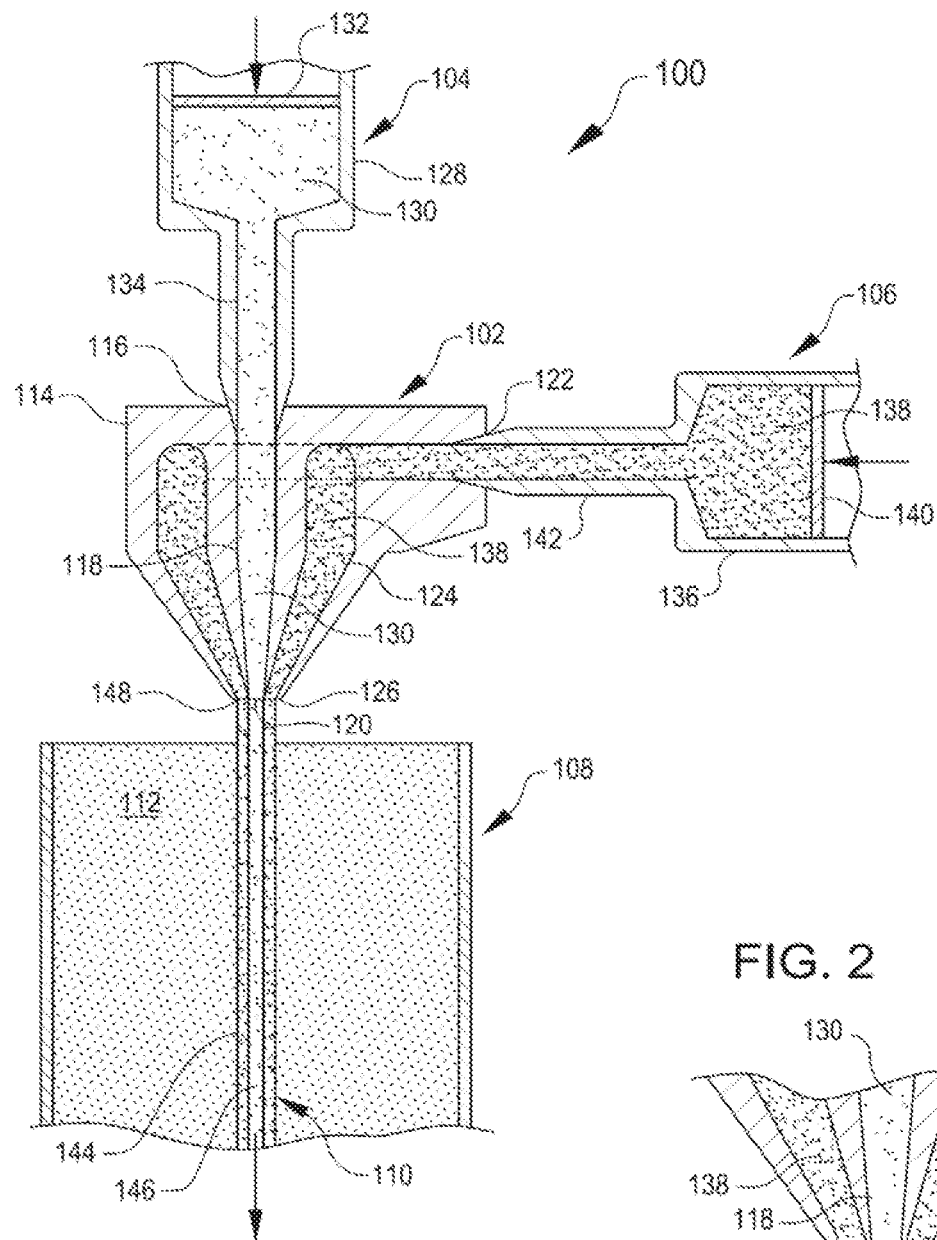
FIG. 1 is a simplified side section schematic showing a hydrogel extrusion assembly that includes a coaxial nozzle.

Herein are described two general methods for the fabrication of tubular hydrogel constructs through the use of two types of nozzles (i.e., a concentric nozzle and a bell-shaped nozzle). According to various embodiments of the present invention, a tubular hydrogel structure (or coaxial hydrogel structure) can be formed by co-extruding at least two hydrogels through a coaxial nozzle, as shown in FIG. 1. FIG. 1 is a simplified side section schematic showing a hydrogel extrusion assembly 100 that includes a coaxial nozzle 102.

A concentric nozzle design can include an apical inlet 116 in line with the axis of extrusion which feeds the inner conduit 118; and a lateral inlet 122 oriented perpendicular to the axis of extrusion which feeds the outer conduit 124 (i.e., the space defined by the annular cross-section between the wall of the inner conduit and the outermost wall of the nozzle). In use, the coaxial nozzle 102 is connected with a first pneumatic syringe 104 that includes a first reservoir 128 containing a hydrogel solution 130. The first pneumatic syringe 104 is fluidly connected with the apical inlet 116 by a first conduit 134. Coaxial nozzle 102 is simultaneously connected with a second pneumatic syringe 106 that includes a second reservoir 136 containing a second, cross-linkable hydrogel solution 138. The second pneumatic syringe 106 is fluidly connected with the lateral inlet 122 by a second conduit 142. Depending on the type of hydrogel construct to be extruded, the first hydrogel solution 130 may or may not also be a cross-linkable hydrogel.

A coaxial hydrogel filament 110 can be extruded from the apical tip 148 of the coaxial nozzle 102 by forcing the first and second hydrogel solutions 130, 138 through the respective inner and outer conduits 118, 125 and out through an inner nozzle outlet 120 and outer nozzle outlet 126 by, e.g., forcing plungers 132, 140 through the first and second pneumatic syringes 104, 106, or by otherwise pressurizing the hydrogel reservoirs 128, 136. Not only the rate of extrusion, but the thickness and dimensional parameters of the coaxial hydrogel filament 110 can be influenced by the applied pressure and particularly the relative rate at which each of the first hydrogel solution 130 and second hydrogel solution 138 are coextruded. As detailed below, increasing the relative rate of extrusion of the second, cross-linkable hydrogel solution 138 generally results in thicker walls of the coaxial hydrogel filament 110 and any resulting tube. At the time of extrusion, the coaxial hydrogel filament 110 may be delicate, and can be extruded into a container 108 containing a supportive fluid 112.

The specific dimensions of the inner nozzle outlet 120 and outer nozzle outlet 126 can vary depending on the desired dimensions of the coaxial hydrogel filament, but are typically on the order of about 0.010-1000 mm in diameter (for the inner nozzle outlet 120) and about 0.030-2000 mm in outer diameter (for the outer nozzle outlet 126). The inner nozzle outlet 120 and outer nozzle outlet 126 may be separated by a narrow band of the nozzle body 114, but typically, the outer nozzle outlet 126 converges on the inner nozzle outlet 120 so that separation is minimal.

Figure 2:
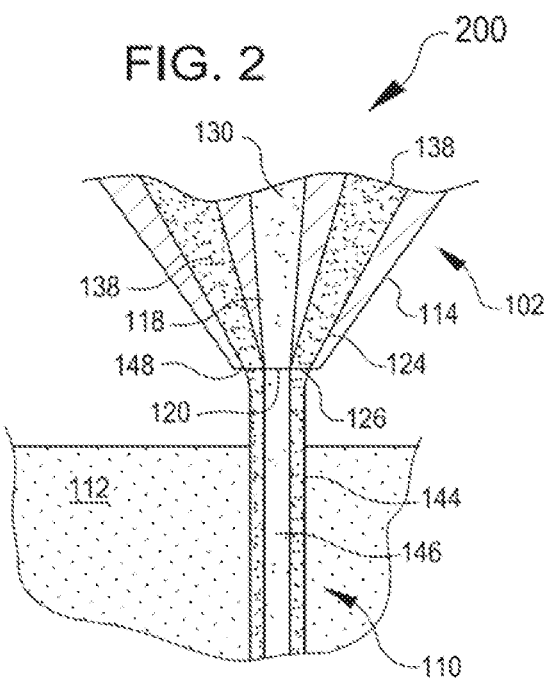
FIG. 2 is a side section schematic showing the coaxial nozzle of FIG. 1 in greater detail along with an extruded hydrogel structure.

FIG. 2 is a side section schematic showing the coaxial nozzle 102 of FIG. 1 in greater detail, with emphasis on a tip portion 200 of the nozzle along with an extruded hydrogel structure made up of a coaxial hydrogel filament 110. As shown, the first hydrogel solution 130 is forced through the inner conduit 188 in the nozzle body 114, exits at the inner nozzle outlet 120 and becomes a supportive, inner hydrogel filament 126 of the coaxial hydrogel filament 110. The second, cross-linkable hydrogel solution 138 is forced through the outer conduit 124, exits at the outer nozzle outlet 126, where it forms a tubular outer layer 144 as a sheathe around the inner hydrogel filament 146 in the coaxial hydrogel filament 110. As the cross-linkable hydrogel solution 138 is extruded from the coaxial nozzle 102, it undergoes shear-thinning, resulting in temporary reduction in viscosity enabling it to form a uniform layer around the supportive inner hydrogel filament 146. Upon exiting the nozzle assembly 102, the cross-linkable hydrogel solution 138 quickly gels, forming the semi-durable tubular layer 144.

Figure 3:
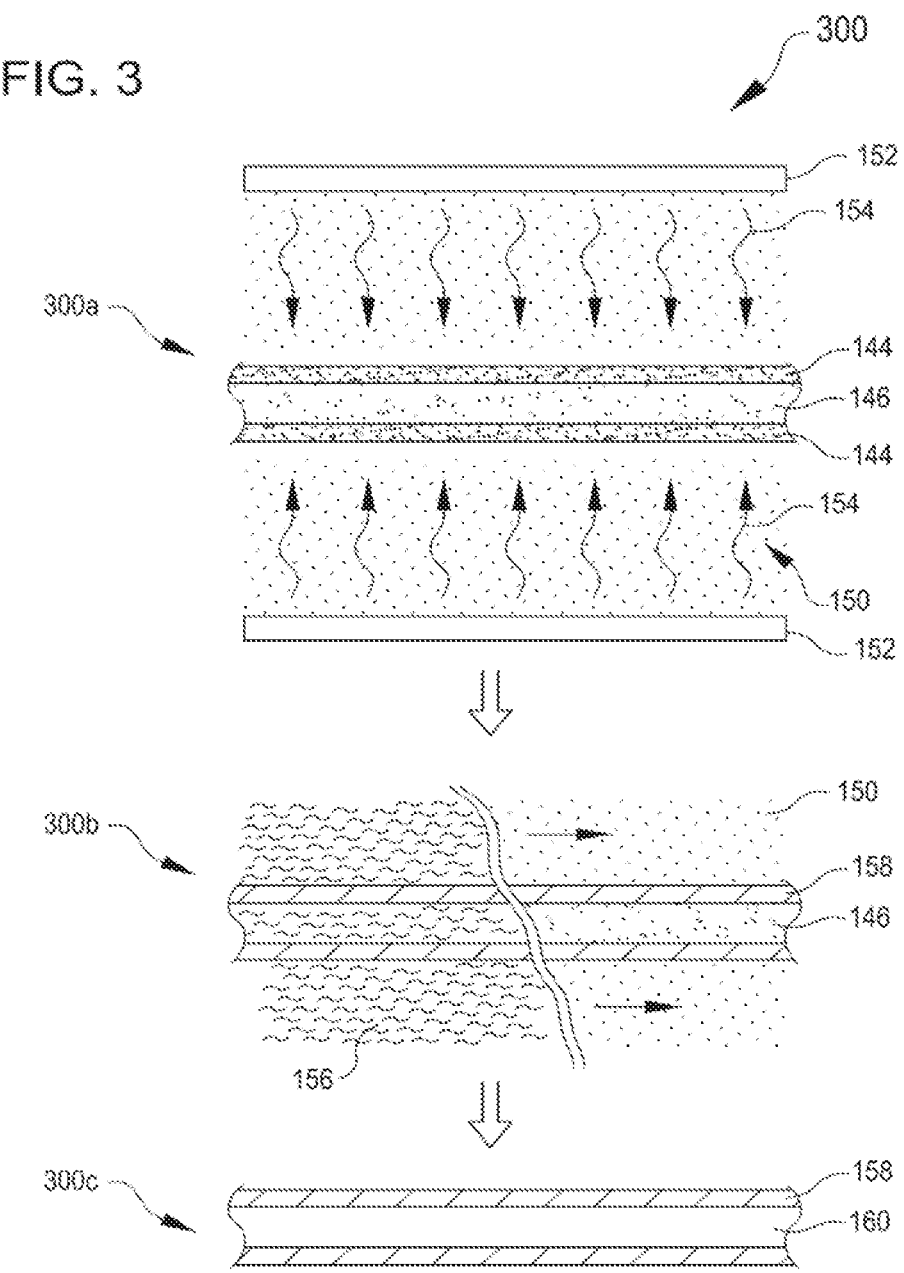
FIG. 3 is a simplified side section schematic illustrating steps in a first example process for preparing a hydrogel tube.

The semi-durable tubular outer layer 144 can subsequently be cured to stabilize the layer, create a durable hydrogel tube, and permit removal of the supportive inner hydrogel filament 146. FIG. 3 is a simplified side section schematic illustrating steps in a first example process 300 for preparing a durable hydrogel tube, according to various embodiments of the present disclosure. In a curing step 300a, the coaxial hydrogel filament 110 can be exposed to UV light 154 via emitters 152. This curing stage can be performed while the coaxial hydrogel filament 110 rests in a supportive solution 150, or can be conducted in open air, depending on the size and durability of the filament. The tubular outer layer 144, composed of a photo-cross-linkable hydrogel, will undergo chemical cross-linking in its polymer structure resulting in a durable and water-insoluble hydrogel tube 158.

In a second step 300b, the coaxial hydrogel filament 110, including the now-insoluble hydrogel tube 158, can be washed with a rinse 156 made up of, e.g., excess water or with phosphate-buffered saline (PBS) to re-dissolve the supportive inner hydrogel filament 146. In a third step 300b, excess water/PBS can be removed from the durable hydrogel tube 158 leaving behind a hollow lumen 160.

Loading and Sealing of Tubular Constructs

The durable hydrogel tubes (e.g. tube 158, FIG. 3) formed by the extrusion methods described herein can be used for a variety of applications by loading the hydrogel tubes to form tubular constructs with, e.g. live cells or live organisms, and sealing the tubular constructs. It will be understood, however, that methods of loading and sealing tubular hydrogel constructs can be applied to both small-bore hydrogel tubes (e.g., tubes on the order of less than 1 mm, less than 2 mm, or less than 5 mm) formed by coaxial extrusion methods (FIGS. 1-2), or applied to large-bore hydrogel tubes (e.g., tubes having inner diameters of more than 5 mm, more than 10 mm, or larger), which may be formed by coaxial extrusion methods or by bell-nozzle methods (see, e.g., FIG. 9).

Figure 4:
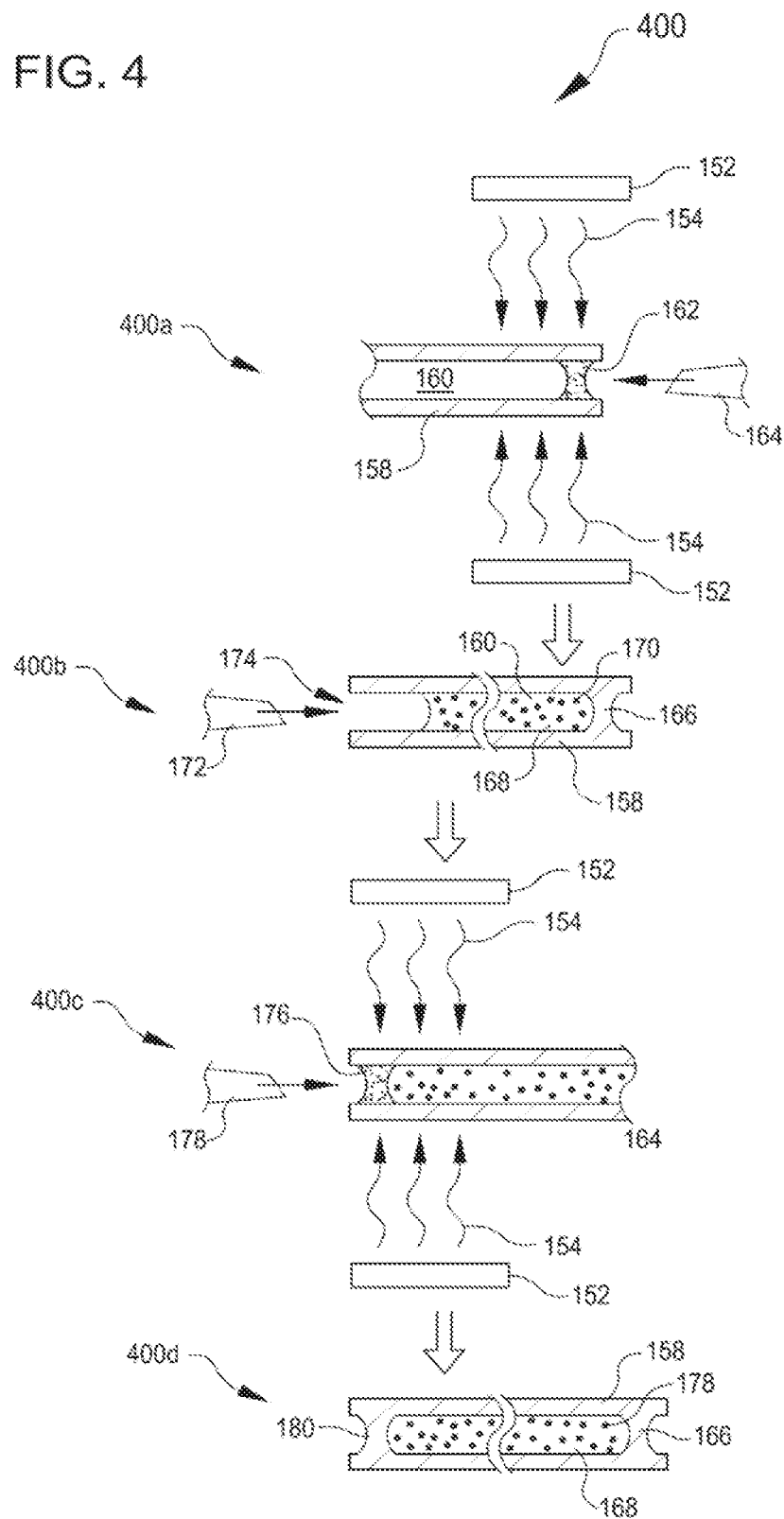
FIG. 4 is a simplified side section schematic illustrating steps in a second example process for preparing a hydrogel tube with a media inclusion.

FIG. 4 is a simplified side section schematic illustrating steps in an example process 400 for preparing a hydrogel tube with a media inclusion. In a first step 400a, a durably hydrogel tube 158 with a hollow lumen 160 can be sealed at one end by injecting a cross-linkable hydrogel plug 162 into the open end via a syringe 164 or other suitable method. According to some embodiments, preparing a suitably clean open end may require cutting the hydrogel tube 158. The hydrogel plug 162 can then be cured, e.g. by exposure to UV light 154 by an emitter 152 to form a cross-linked hydrogel cap 166.

In a second step 400b, the lumen 160 can be filled with media 168, e.g. by way of a second syringe 172 through an open end 174. The media 168 may include a suspension of microorganisms 170, biologically active materials, or other suitable inclusion. In a third step 400c, the lumen 160 can be sealed by the inclusion of a second cross-linkable hydrogel plug 176, which may be deposited via syringe 178 and subsequently cured by exposure to UV light 154 to form a second cross-linked hydrogel cap 180. Finally, in a fourth step 400d, the sealed, media containing hydrogel construct formed in the durable hydrogel tube 158 can be used.

According to various embodiments, the media 168 loaded into the lumen 160 of the hydrogel tube 158 can be a liquid or a gel, including a hydrogel. The loading of liquids or gels into the lumens of tubular constructs via post-fabrication-injection or coextrusion provides a novel approach to (a) the manufacturing or 3D printing of hydrogel-based composite-filaments and (b) the encapsulation or immobilization of cells and microorganisms. In some embodiments, a media-containing hydrogel construct can be used to immobilize and maintain microorganisms for, e.g., visualization, storage, or other clinical or scientific use. According to some other embodiments, a media-containing hydrogel construct can be used as, e.g. a bioreactor, with contained cells that are capable of performing certain biological functions within the tubular construct, capable of taking in nutrients or reagents that can permeate into the hydrogel tube 158 and creating bioproducts that can permeate out from the hydrogel tube. Examples of products that can be produced include metabolites, antibiotics, pharmaceuticals, hormones, chemical feedstocks, peptides, proteins, enzymes, and vaccines.

Figure 5:
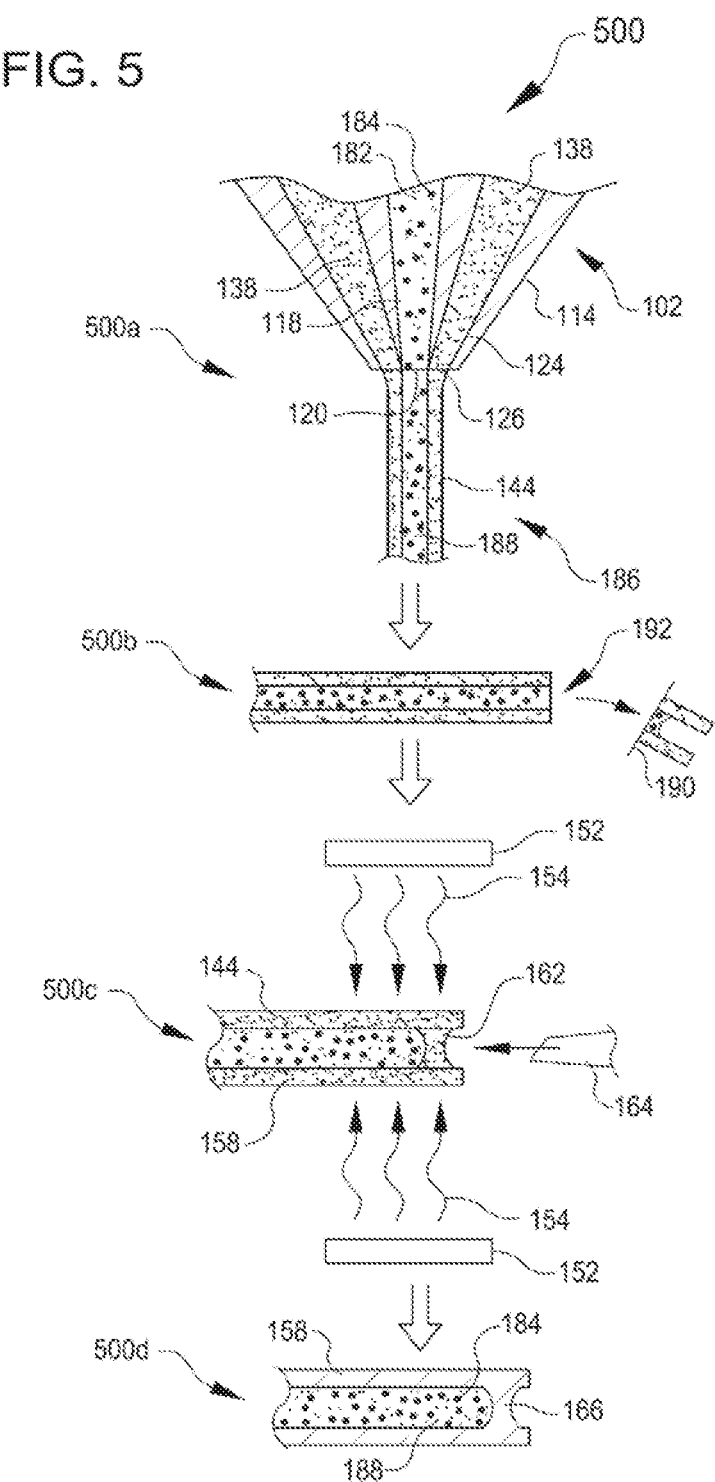
FIG. 5 is a simplified side section schematic illustrating steps in a third example process for preparing a hydrogel tube with a hydrogel inclusion.

In addition to methods of adding cells and microorganisms to existing hydrogel tubes, cells and microorganisms can also be co-extruded and fixed within an inner hydrogel filament and fixed therein. For example, FIG. 5 is a simplified side section schematic illustrating steps in a third example process 500 for preparing a hydrogel tube with a hydrogel inclusion. In a first step 500a, according to various embodiments, an organism-containing coaxial hydrogel filament 186 can be extruded in a similar process to that described above with reference to FIGS. 1-2 for extruding coaxial hydrogel filament 110. A media 182 that includes a hydrogel and containing microorganisms or cells 184 can be co-extruded from an inner nozzle outlet 120 while a cross-linkable hydrogel 138 is extruded from an outer nozzle outlet 126. The hydrogel media 182 is extruded as a cell-containing hydrogel inner filament 188 sheathed by a tubular outer layer 144, forming a cell-impregnated extruded hydrogel filament 186.

In a subsequent, second step 500b, a clean end 192 of the cell-impregnated extruded hydrogel filament 186 can be opened by cleaving 190 the filament. The open end 192 can then be plugged with a cross-linkable hydrogel solution 162 via a syringe 164, and cured, e.g. by UV light 154 (step 500c) to form a cured hydrogel cap 166 that seals a cell-loaded cured hydrogel tube 158, containing a suspension of the cell containing hydrogel inner filament 188 and cells 184.

Preparing Hydrogel Tubes with Luminal Cell Culture

Figure 6:
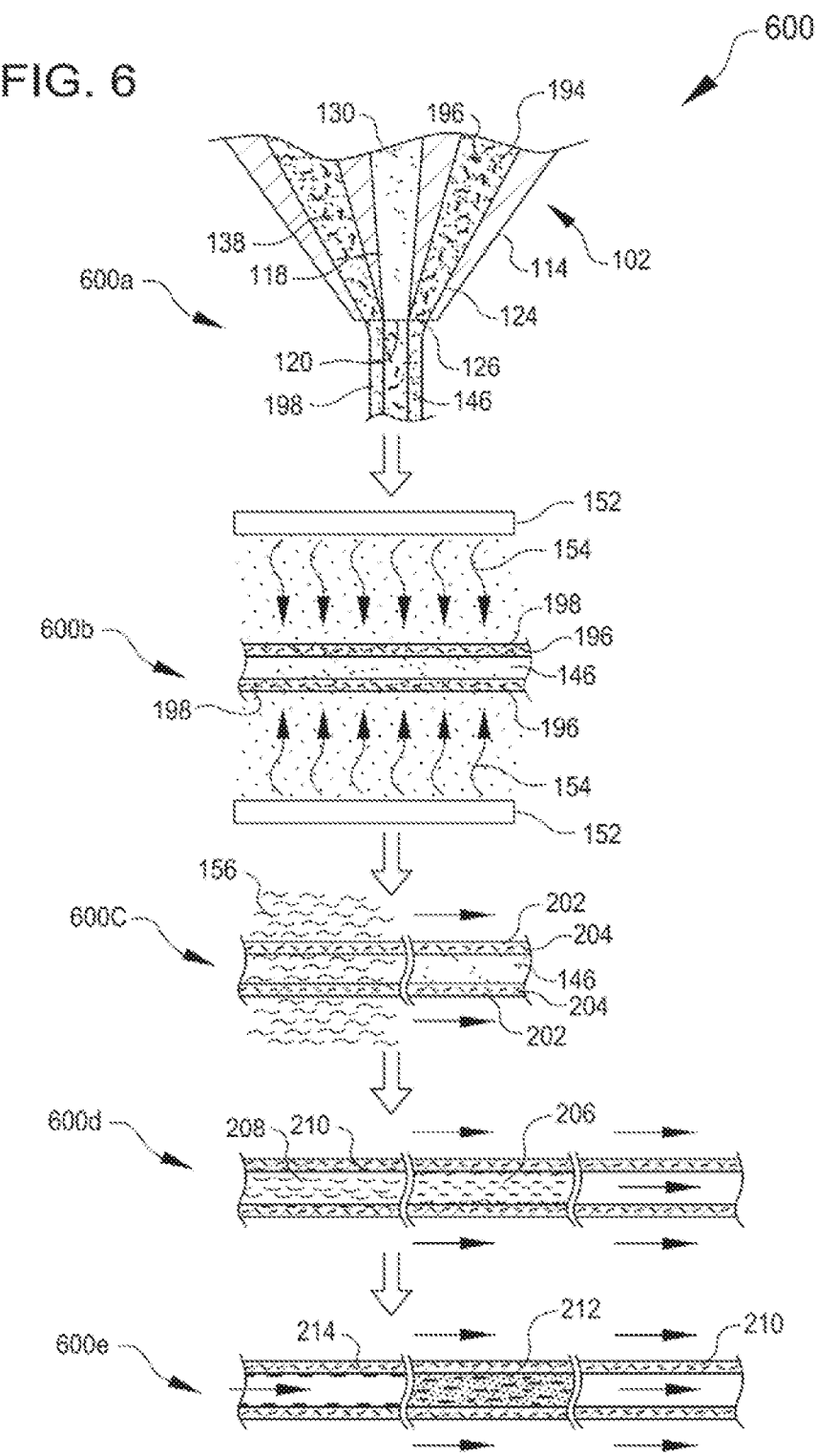
FIG. 6 is a simplified side section schematic illustrating steps in a fourth example process for preparing a hydrogel tube with embedded growth substrate for luminal cell culture in the hydrogel tube.

FIG. 6 is a simplified side section schematic illustrating steps in an example process 600 for preparing a hydrogel tube with embedded growth substrate for luminal cell culture in the hydrogel tube. In a first step 600a, a collagen loaded cross-linkable hydrogel tube 198 can be formed by coextruding a cross-linkable hydrogel solution 194 containing a collagen suspension 196, with a hydrogel solution 130, from a coaxial nozzle assembly 102. In a second step 600b, the collagen-loaded cross-linkable hydrogel tube 198 can be cured (e.g., by UV light 154) while supported by the inner, supportive hydrogel filament 146.

In a third step 600c, the collagen-containing cross-linked tube 202, including embedded collagen suspension 204, can be freed by dissolving the inner, supportive hydrogel filament 146 by a rinse 156 that can include, e.g., excess water or an aqueous solution. In a fourth step 600d, the collagen-containing cross-linked tube 202 can be treated to embed collage suspension on the luminal surface thereof by, e.g. partially dehydrating the cross-linked tube 202, rehydrating the cross-linked hydrogel tube 202 with a collagen-containing solution 206, and subsequently rinsing the cross-linked tube with, e.g., an ammonia wash 208 to cause a layer of collagen 210 to form on the luminal surface of the cross-linked hydrogel tube 202.

The cross-linked tube 202 with a bound, luminal collagen layer 210 can be used to support various types of cell cultures including, but not limited to, human tissue cultures. For example, according to some embodiments, as shown in step 600e, the cross-linked tube 202 can be treated with media 212 containing a cell culture (e.g., human endothelial cells, or other suitable cells), which can then bond with the collagen layer 210 and form colonies 214 thereon.

Preparing Hydrogel Tubes with Fixed, Internal Cell Culture

Figure 7:
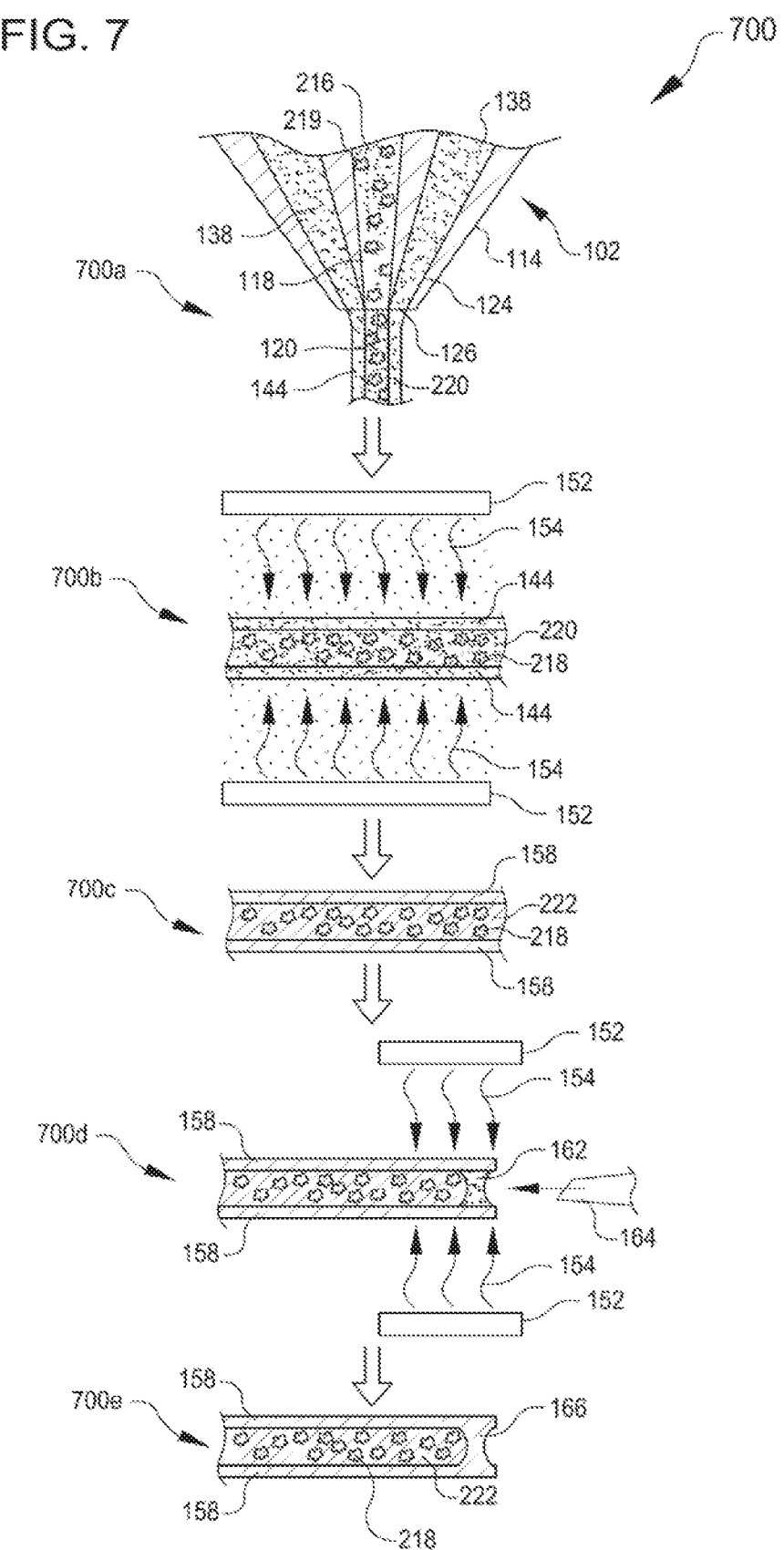
FIG. 7 is a simplified side section schematic illustrating steps in a fifth example process for preparing a hydrogel tube with a cross-linked hydrogel inclusion.

FIG. 7 is a simplified side section schematic illustrating steps in a fifth example process 700 for preparing a hydrogel tube with a cross-linked hydrogel inclusion containing suspended cells. In a first step 700a, according to various embodiments, an organism-containing coaxial and cross-linkable hydrogel filament 220 can be extruded in a similar process to that described above with reference to FIGS. 1-2 for extruding coaxial hydrogel filament 110. Cross-linkable hydrogel media 216 containing microorganisms or cells 218 can be co-extruded from an inner nozzle outlet 120 while a cross-linkable hydrogel 138 is extruded from an outer nozzle outlet 126. The inner cross-linkable hydrogel media 216 is extruded as a cell-containing hydrogel inner filament 220 sheathed by a tubular outer layer 144, forming a cell-impregnated extruded hydrogel filament.

In a subsequent, second step 700b, the cell-impregnated extruded hydrogel filament can be cured, e.g. by UV light 154 to form a cured and durable hydrogel tube 158 surrounding a cured hydrogel inner filament 222, that contains and fixes the suspension of cells or organisms 218 therein (step 700c). According to some embodiments, the cured hydrogel inner filament 222 can be further isolated from an external environment by additionally capping the ends of the durable hydrogel tube 158 by, e.g., inserting a plug of cross-linkable hydrogel 162 via syringe 164 (step 700d) and curing the plug to form a cured hydrogel cap 166 (step 700e).

Continuous Methods of Fabricating Hydrogel Tubes

Figure 8:
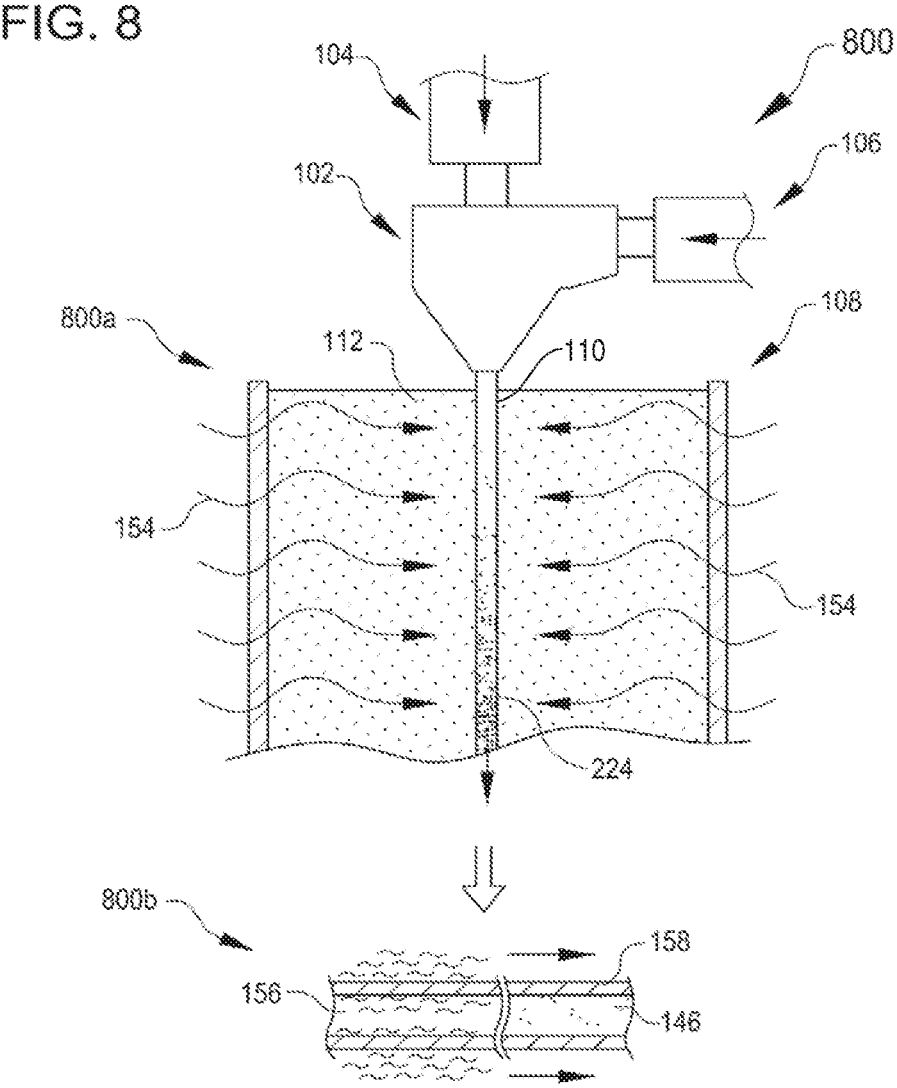
FIG. 8 is a simplified side section schematic showing a continuous extrusion/curing process for preparing a hydrogel tube.

Hydrogel tubes described above with reference to FIGS. 1-2 can be formed by either discontinuous or continuous processes. For example, FIG. 8 illustrates a first example of a continuous forming process 800 for forming a cured hydrogel tube 158, in accordance with various embodiments of the present disclosure. In a first stage 800a of the continuous forming process 800, a first syringe 104 containing a hydrogel solution and a second syringe 106 containing a cross-linkable hydrogel solution are connected with a coaxial nozzle assembly 102 and pressurized to force the two hydrogels through the coaxial nozzle assembly, in order to form a coaxial hydrogel filament 110, similar to methods described above with reference to FIGS. 1-2. The uncured, coaxial hydrogel filament 110 can be suspended in a supportive fluid medium 112 and subjected in-situ to UV light 154 during the extrusion process, by which the outer portion of the coaxial filament 110 formed by the cross-linkable hydrogel solution is cured to form a cured coaxial hydrogel filament 224, in which the outer layer is a water insoluble, cross-linked hydrogel tube 158 containing a soluble inner hydrogel filament 146. In a second stage 800b of the forming process, the cured coaxial hydrogel filament 224 can be washed with a solvent rinse 156, such as but not limited to excess water or PBS, for dissolving the inner hydrogel filament 146, leaving behind only the hydrogel tube 158.

Figure 9:
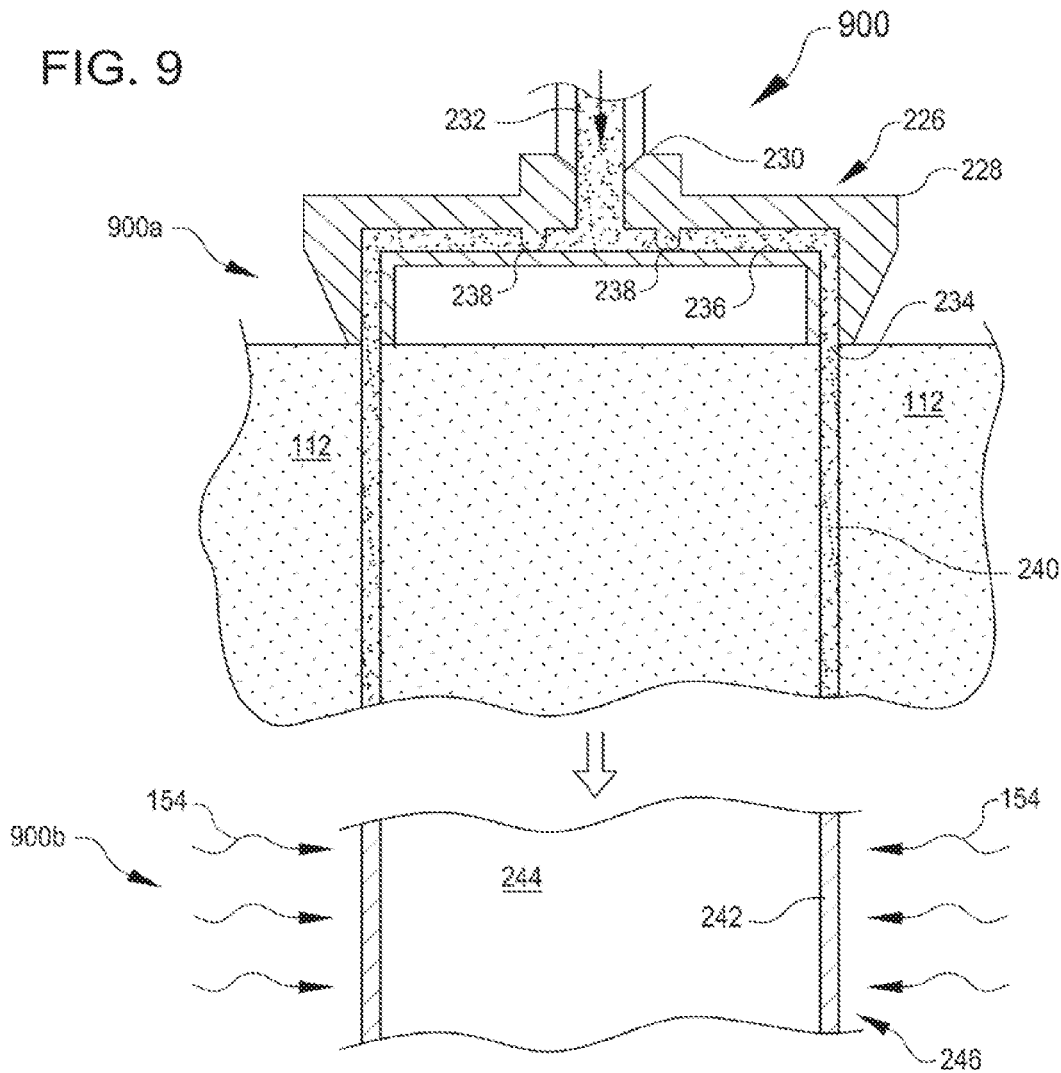
FIG. 9 is a simplified side section schematic showing an extrusion/curing process for preparing a large-bore hydrogel tube.

FIG. 9 illustrates a second example of a continuous forming process 900 for forming a cured hydrogel tube 242 based on a bell-shaped nozzle process, in accordance with various embodiments of the present disclosure. In a first stage 900a, a cross-linkable hydrogel solution 232 is forced through a bell nozzle 226 from a nozzle inlet 230, through an inner channel 236 within a nozzle body 228, and out through an annular nozzle outlet 234. Connective elements 238 are bypassed by the hydrogel solution 232 within the inner channel 236. The bell nozzle can be characterized by a diameter of the nozzle outlet (for annular nozzle outlets) ranging from about 10-20 mm, or larger. The cross-linkable hydrogel solution 232 shear thins during extrusion, and gels when no longer subject to shear beyond the nozzle outlet 234 forming a large-bore uncured hydrogel tube 240. The hydrogel tube 240 can be suspended in air, or may be extruded into a supportive fluid 112 that can help to support the weight of the hydrogel tube during extrusion and prior to the curing step. In a second stage 900b, the uncured hydrogel tube 240 can be cured by subjecting the hydrogel tube to UV light 154 to form a cured hydrogel construct 246 that includes a durable cross-linked hydrogel tube 242 and open lumen 244.

The bell-shaped nozzle 226 can include a single apical inlet 230 in line with an axis of extrusion which feeds the single annular conduit 236; this annular conduit is analogous in function to the outer conduit (126, FIG. 1) in the concentric nozzle design. Nozzles conforming to these general geometries, but of varying dimensions were fabricated for the production of tubes with a range of diameters and wall thicknesses.

Fabrication of 3D Printed Nozzle Assemblies for Hydrogel Extrusion

Custom print head nozzles for the extrusion, or extrusion-based-3D-printing, of coaxial filament and tubular hydrogel constructs were digitally prototyped using computer-aided design (CAD) software and 3D printed using a digital light projection (DLP) 3D printer. Two general designs were employed for the nozzles: (1) a dual-inlet nozzle with concentric inner and outer conduits was fabricated for use in the production of small-medium diameter tubes (FIGS. 1-8), and (2) a bell-shaped single-inlet nozzle with a single annular conduit was fabricated for use in the production of large diameter tubes (FIG. 9).

The DLP 3D printer used in the fabrication of the nozzles (Autodesk Ember) is reported as having 50 micron XY resolution and 405 nm, 5W laser specifications. The photopolymer resin used was Autodesk's Standard Clear (PR48) resin [refer to formulation]. Basic print parameters were as follows: nozzles were printed with zero build surface standoff and without the use of printed support structures. Layer height was set to 50 microns. Light exposure time was set to 8 s, 5 s, and 2.2 s for the first, second-fifth, and all remaining layers, respectively. Separation and approach slide velocities were universally set to 3 rpm for all layers. All additional print parameters were kept at their default values. After printing, nozzles were washed for five minutes with technical grade isopropyl alcohol to remove residual photopolymer resin. Nozzles were then purged and dried with pressurized air and post-cured on a reflective aluminum surface under a dual-bulb (365 nm, 600 m W) UV lamp for 30 minutes. After post-cure, 14-gauge by ½ inch blunt-tip syringe needles with stainless steel cannulas (Metcal) were affixed to printed nozzle inlets with J-B Weld MarineWeld adhesive. Prior to affixing, the cannulas were ground to 5 mm in length using an aluminum oxide abrasive disc; they were then deburred and washed with isopropyl alcohol. The adhesive was left to cure for 24 hours at ~20° C. before a final wash and use of the nozzles.

Figure 10:
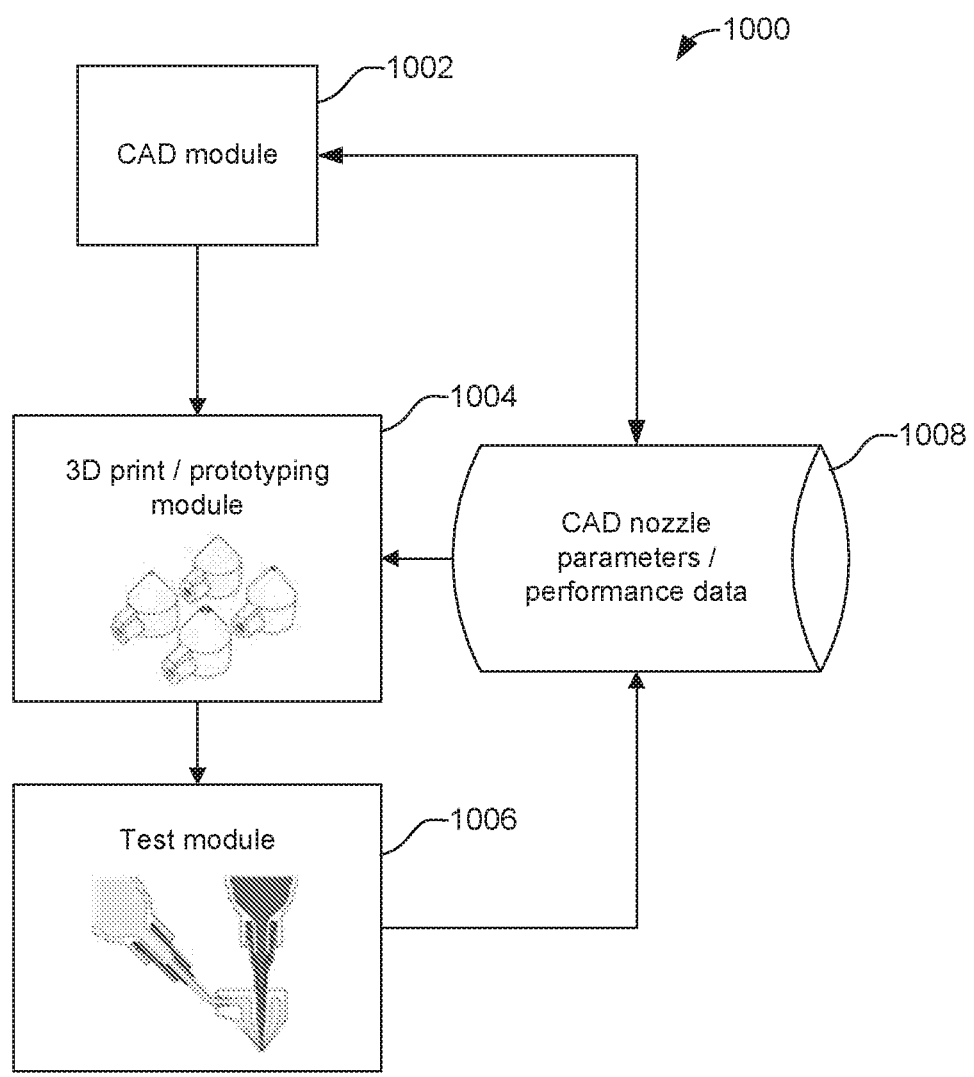
FIG. 10 is a simplified block diagram illustrating an example system for iterative development of 3D-printed nozzle geometries.

One advantage of utilizing 3D printed or rapid-prototyped nozzles for extrusion of hydrogel structures is that modifications to the design of the nozzle can be performed iteratively to achieve different results (e.g., shaped hydrogel structures, varying tube diameters, lumen diameters, and wall thicknesses, among others). FIG. 10 is a simplified block diagram illustrating an example system 1000 for iterative development of 3D-printed nozzle geometries, in which a CAD module 1002 can be used to prepare and store an initial CAD nozzle design. The CAD nozzle design can be fabricated quickly by way of a 3D printing module 1004, based on parameters provided via the CAD module 1002 and/or a data store 1008 containing nozzle parameters. Suitable physical candidate nozzles, after production, can be tested in a test module 1006 for measuring, e.g., lumen diameter, wall thickness, tube diameter, patentcy, and/or other suitable criteria for assessing a product hydrogel structure. Said performance criteria can then be stored in a data store 1008 and accessed by the CAD module for iteratively developing variations on each successive nozzle design. According to some embodiments, the process of collecting CAD nozzle parameters and related performance data can be distributed, with the data store 1008 configured to accept input from multiple test modules 1006 and to provide access to multiple CAD modules 1002, which are not necessarily co-located.

FIG. 11 illustrates an example process 1100 for iteratively developing 3D-printable nozzle geometries, in accordance with the various embodiments described above with reference to FIGS. 1-10. Some or all of the process 1100 (or any other processes described herein, or variations, and/or combinations thereof) may be performed under the control of one or more computer systems configured with executable instructions and may be implemented as code (e.g., executable instructions, one or more computer programs, or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

In accordance with various embodiments, a set of initial 3D nozzle parameters can be generated or retrieved corresponding to, e.g. a coaxial nozzle or bell nozzle geometry. (Act 1102) Suitable 3D nozzle parameters can include the type of nozzle geometry (e.g., coaxial, bell), the size and shape of the nozzle outlets (e.g., circular, star-shaped, etc.), the diameters of the axial inner nozzle and/or annular outer nozzle, the relative diameters of the axial inner nozzle and annular outer nozzle with respect to each other, the inner slope or camber of each inner wall of the annular outer nozzle, the inner slope or camber of the wall of the axial inner nozzle, and other suitable physical characteristics. According to some embodiments, the initial 3D nozzle parameters can be selected from a subset of 3D nozzle shapes that have undergone virtual testing by way of finite element (FE) analysis, or other suitable numerical computational analysis, usable to simulate fluid flow through a nozzle.

Based on an initial set of nozzle parameters, a CAD nozzle can be generated for rapid prototyping or 3D printing (Act 1104) and then printed (Act 1106), typically in multiples to enable repeat testing. Note that the generated CAD nozzle can also be uploaded (e.g. to a cloud service or local computing system) and subsequently used by multiple or potentially many client devices to then access and 3D print nozzles based on the CAD model. The performance of any given printed nozzle can be tested and rated based on hydrogel tube criteria (e.g., lumen diameter, wall diameter, uniformity) by measuring the parameters of hydrogel tubes extruded using a given 3D printed nozzle. (Act 1108) Performance characteristics prepared in this way can be associated with particular nozzle parameters. (Act 1110)

The nozzle parameters and associated performance characteristics can be used as a basis for incremental modification of the CAD nozzle's specific dimensions, and the process can be performed iteratively by preparing new CAD nozzles with incremental changes, and developing performance data for each subsequent set of nozzle parameters. (Act 1112) The developed performance characteristics and associated nozzle parameters can be stored, or in some embodiments uploaded to a cloud service or local server. (Act 1114) The performance characteristics can include, e.g., the physical dimensions and reliability of the extrusion process for any suitable number of hydrogel formulations, based on any suitable number of experimental conditions (e.g., extrusion temperature, storage temperature, extrusion pressure(s), etc.). According to some embodiments, the iterative process can be performed in parallel in multiple facilities with access to a common data set storing the performance characteristics and associated nozzle parameters.

Performance Characteristics of Small-Bore Hydrogel Tubes

Figure 12A:
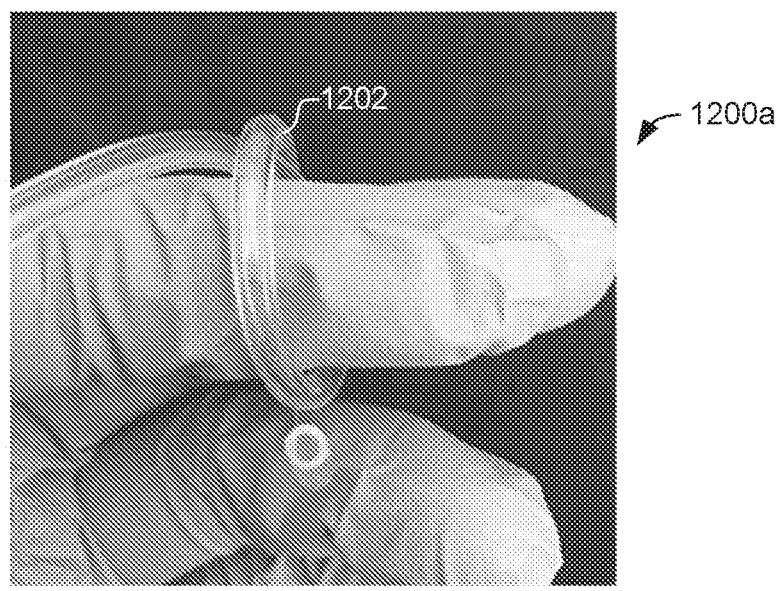
FIGS. 12A and 12B are a pair of images of hydrogel tubes formed via a large-diameter coaxial nozzle, with emphasis on illustrating the flexibility and durability thereof.
Figure 12B:
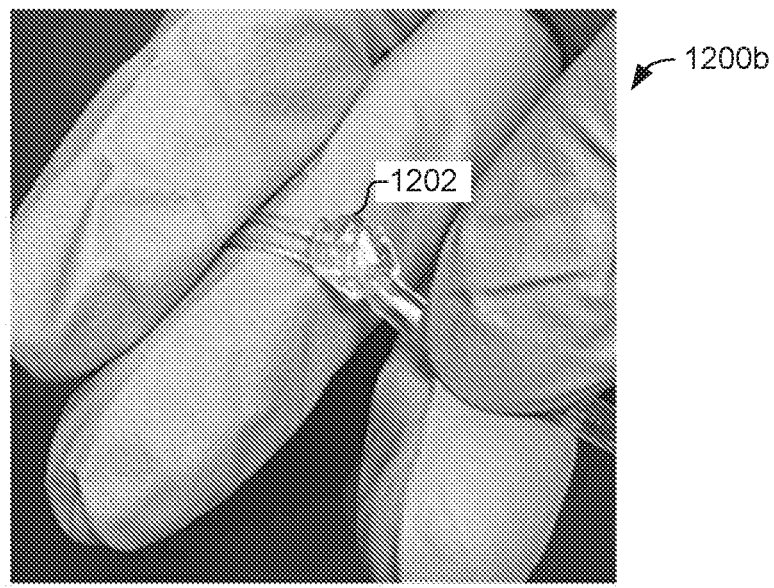

FIGS. 12A and 12B shows a pair of images 1200a, 1200b of a hydrogel tube 1202 formed via a coaxial nozzle having an outer conduit diameter of 2 mm, with emphasis on illustrating the flexibility and durability thereof. Hydrogel tubes produced thereby have good elasticity and toughness. As shown in FIG. 12A, hydrogel tube 1202 can be readily wound without substantial deformation of the lumen. As shown in FIG. 12B, hydrogel tube 1202 has sufficient durability to withstand extreme flexure without breaking.

Figure 13A:
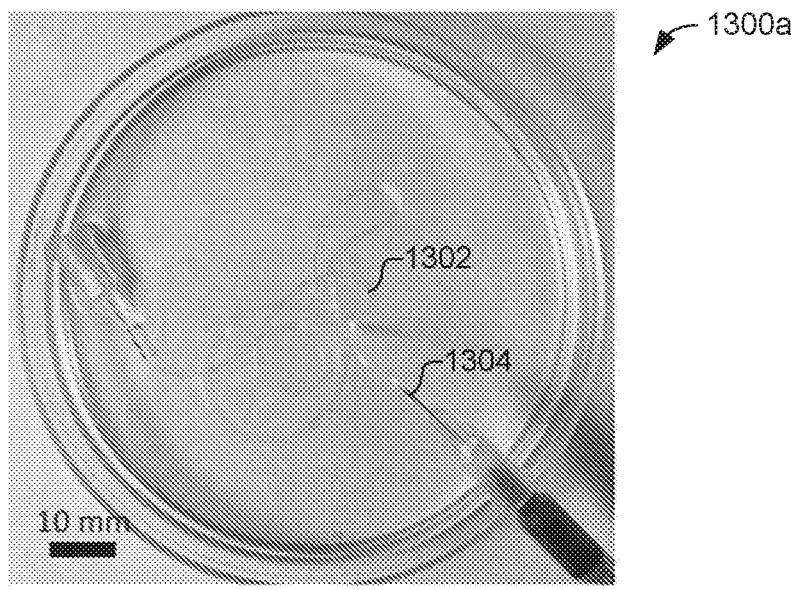
FIGS. 13A and 13B are a pair of images of hydrogel tubes formed via a small-diameter coaxial nozzle, with emphasis on illustrating the flexibility and lumen patency.
Figure 13B:
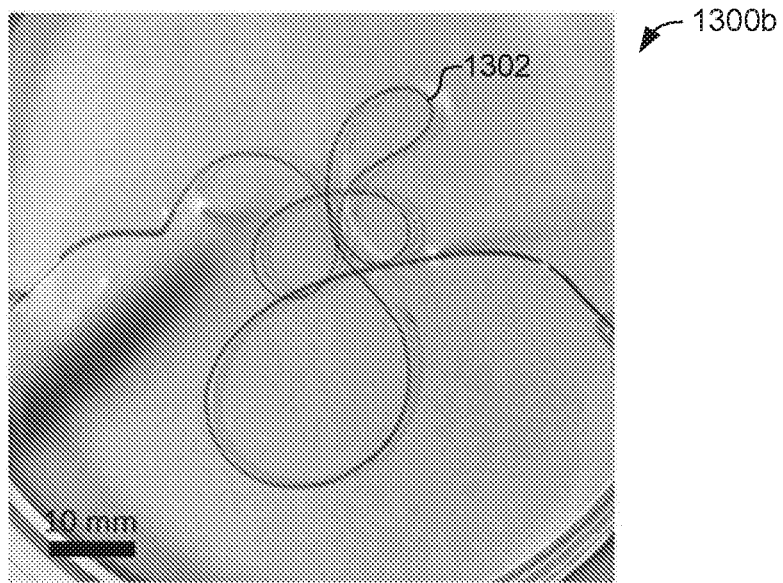

FIGS. 13A and 13B show images of hydrogel tubes formed via a small-diameter coaxial nozzle (0.5 mm outer diameter), with emphasis on illustrating the flexibility and lumen patency. As shown in FIG. 13A, a narrow hydrogel tube 1302 supported by syringe 1304 is highly flexible without undergoing permanent deformation. As shown in FIG. 13B, the same narrow hydrogel tube retains high patency and a highly regular lumen diameter, as shown by the regularity of a stream of dye injected therethrough that has stained the lumen walls.

Figure 14A:
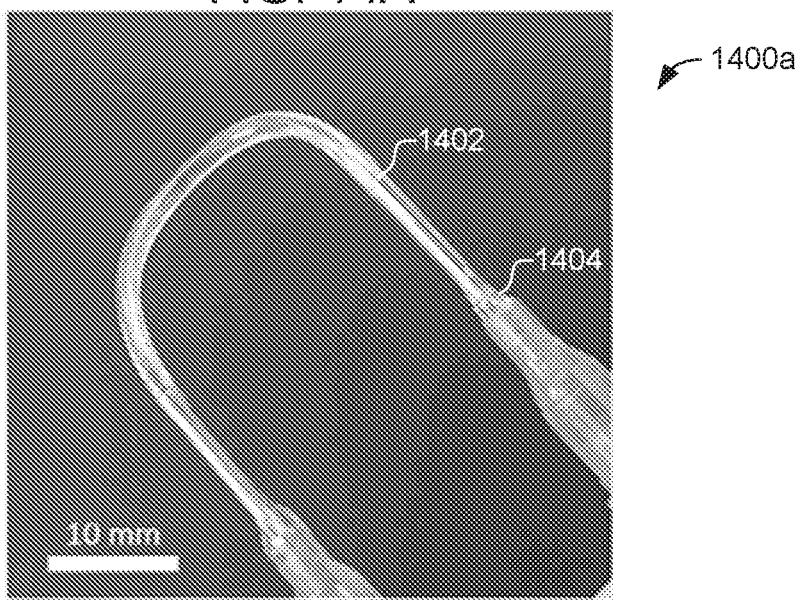
FIGS. 14A and 14B are a pair of images of small-diameter hydrogel tubes formed via a coaxial nozzle, with emphasis on illustrating the flexibility and durability thereof.
Figure 14B:
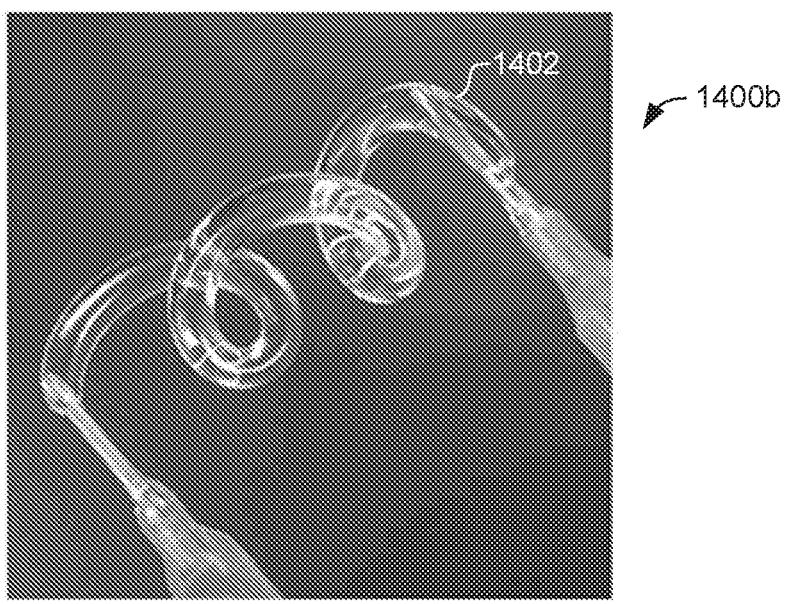

FIGS. 14A and 14B shows a pair of images 1400a, 1400b of a hydrogel tube 1402 formed via a coaxial nozzle, supported on a pair of syringes 1404. As shown in FIG. 14A, hydrogel tube 1402 can be readily straightened and, as shown in FIG. 14B, reversibly twisted without permanently deforming the hydrogel tube.

Figure 15A:
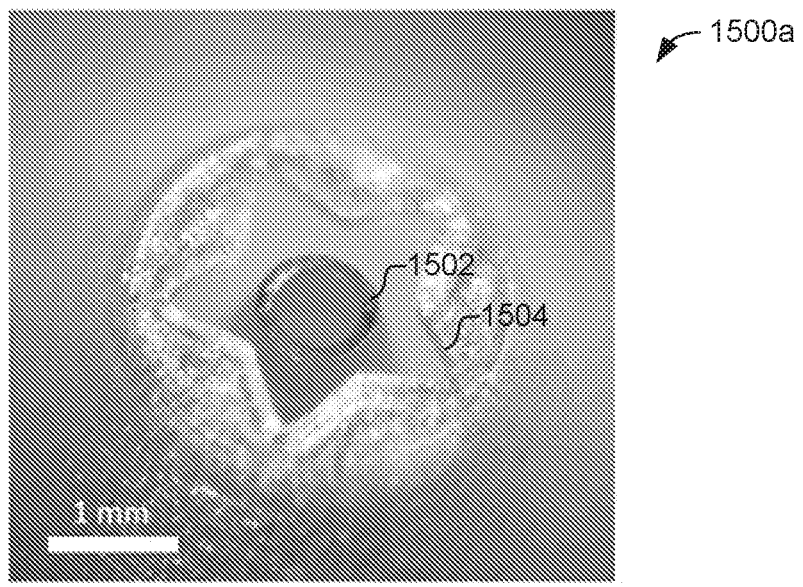
FIGS. 15A and 15B are a pair of images of a star-shaped coaxial nozzle and a cross-sectional geometry of a hydrogel tube formed thereby.
Figure 15B:
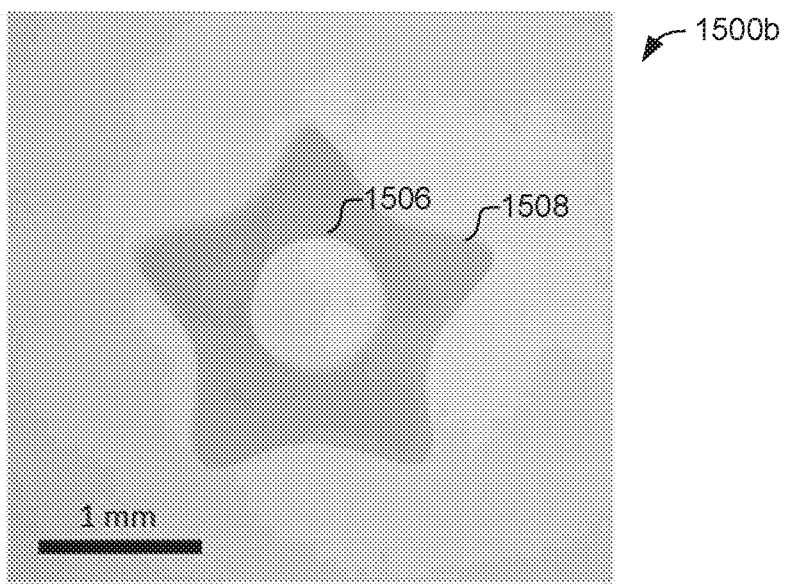

FIGS. 15A and 15B illustrate how variations in the nozzle geometry can be used to generate interesting variations in the hydrogel tube geometry. For example, FIG. 15A shows a nozzle shape 1500a having a star-shaped outer conduit outlet 1504 around a circular inner outlet 1502. As shown in FIG. 15B, the star-shaped outer conduit outlet 1504, when applied to a coaxial extrusion method (FIGS. 1-2) results in a star-shaped tube wall 1508 surrounding a circular lumen 1506.

Figure 16A:
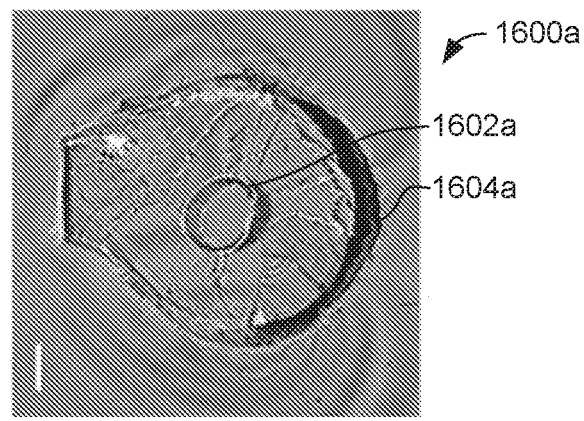
FIGS. 16A, 16B and 16C are a series of images of hydrogel tube cross-sectional geometries corresponding to varying extrusion pressure for a common nozzle.
Figure 16B:
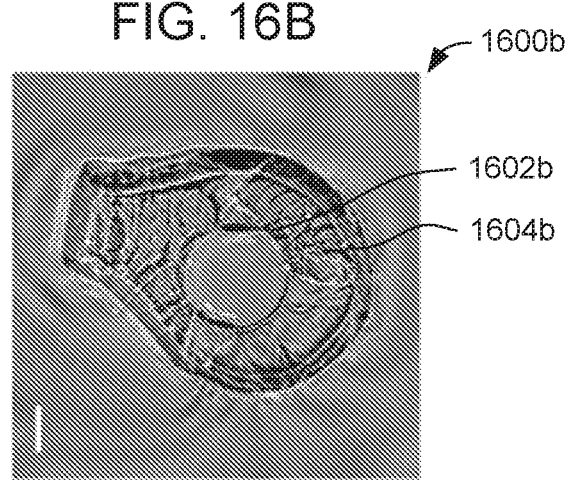
Figure 16C:
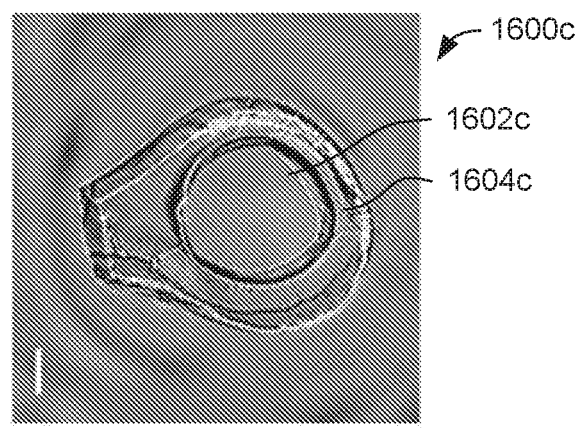

FIGS. 16A, 16B, and 16C are a series of images showing hydrogel tube cross-sectional geometries corresponding to varying extrusion pressure for a common nozzle. FIG. 16A shows a hydrogel tube cross-section 1600a formed by increasing the pressure of the cross-linkable hydrogel solution extruded from the outer nozzle outlet (e.g. outer nozzle outlet 126, FIGS. 1-2) relative to the pressure of the hydrogel solution extruded from the inner nozzle outlet (e.g. inner nozzle outlet 120, FIGS. 1-2). The resulting hydrogel tube has a relatively thick tube wall 1604a surrounding a relatively narrow lumen 1602a. FIG. 16B shows a hydrogel tube cross-section 1600b formed by balancing the pressure of extrusion for the cross-linkable hydrogel solution from the outer nozzle outlet relative to the pressure of extrusion for the hydrogel solution from the inner nozzle outlet, forming a hydrogel tube where the outer wall 1604b and inner lumen 1602b are similar in dimension to the respective outer and inner nozzle outlets. FIG. 16C shows a hydrogel tube cross-section 1600c formed by decreasing the pressure of extrusion for the cross-linkable hydrogel solution from the outer nozzle outlet relative to the pressure of extrusion for the hydrogel solution from the inner nozzle outlet, forming a hydrogel tube where the outer wall 1604c is relatively thin compared to the diameter of the inner lumen 1602c. In this manner, the relative thickness of the hydrogel tube wall and lumen diameter can be tuned independent of the selection of the coaxial nozzle design, by manipulating the relative pressure of extrusion of the hydrogel solutions.

Development of Hydrogel Inks for Extruding Hydrogel Structures

Figure 17:
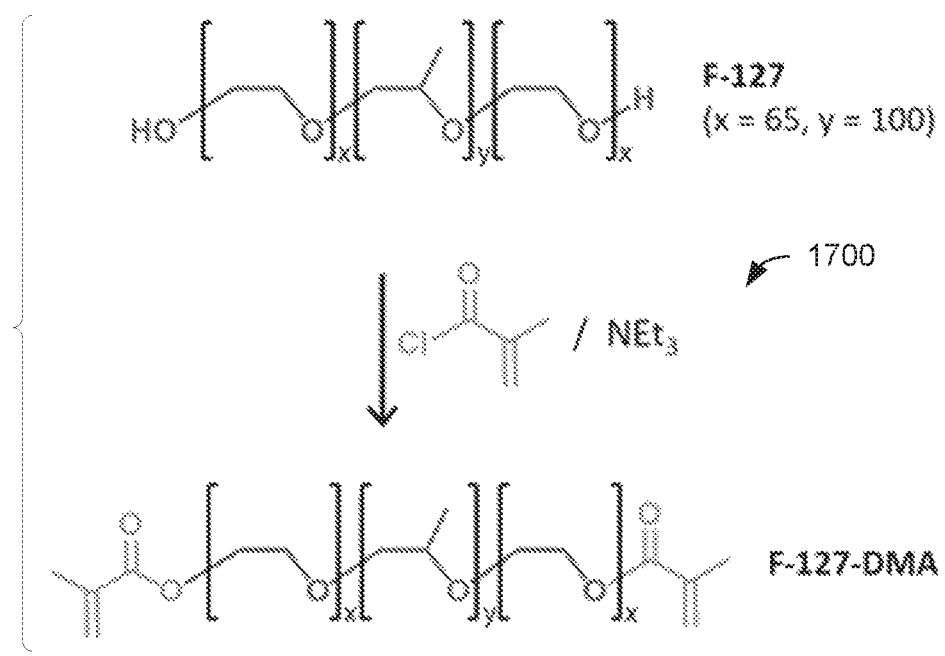
FIG. 17 is a simplified chemical diagram illustrating the chemical structure of hydrogel F127 and synthesis of hydrogel F127-DMA.
Figure 18:
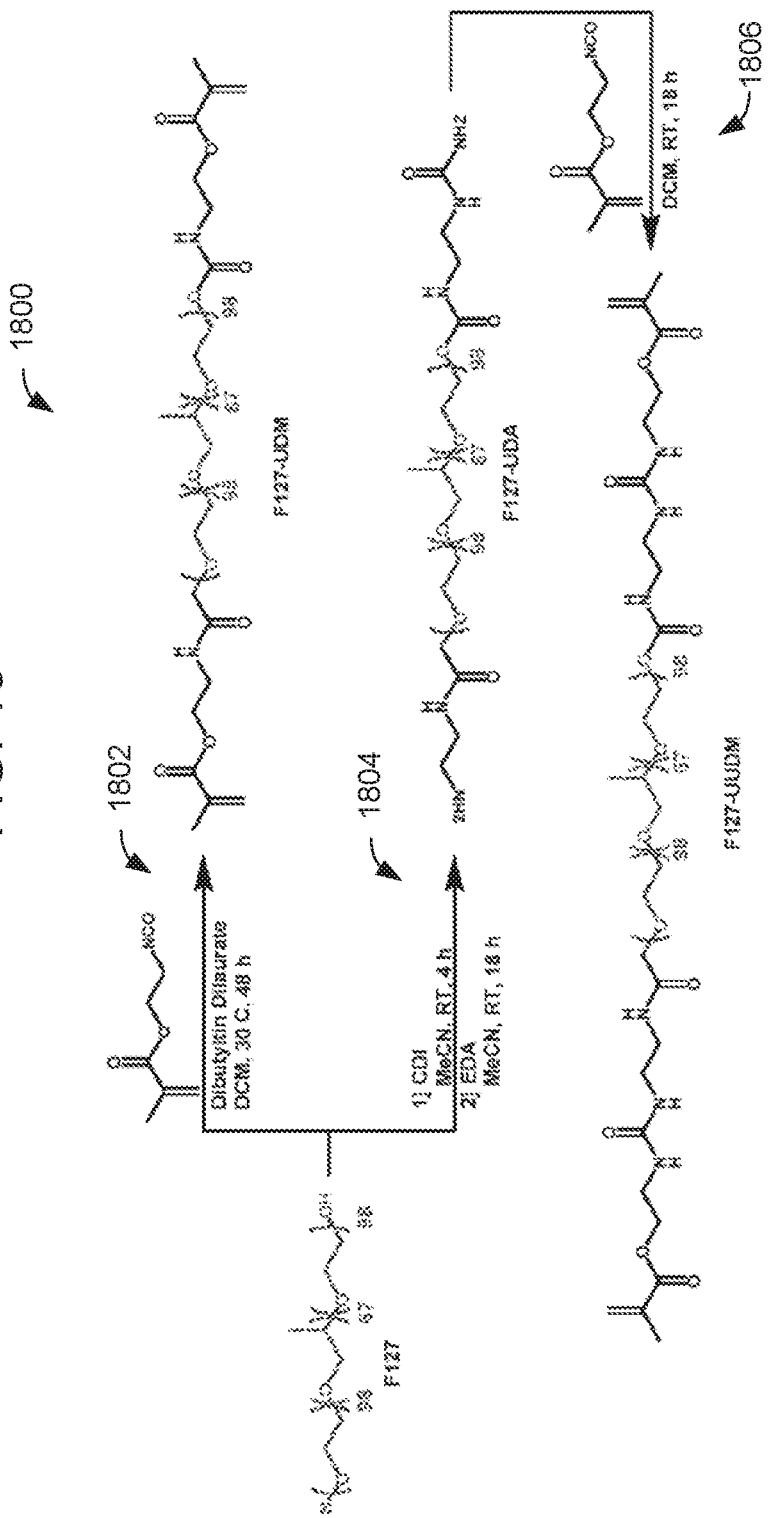
FIG. 18 is a simplified chemical diagram illustrating the chemical structures and synthesis pathways of hydrogel F127-UDM (F127-BUM), F127-UDA, and F127-UUDM.

The hydrogel inks suitable for extrusion or "printing" from the nozzles described above are based on the structure of the polymers shown in FIGS. 17-18. FIG. 17 is a simplified chemical diagram 1700 illustrating the chemical structures of hydrogel F127 and hydrogel F127-DMA, and the synthesis of hydrogel F127-DMA. Methacryloyl chloride is reacted with F127 in the presence of a scavenger base such as triethylamine to afford F127-DMA. FIG. 18 is a simplified chemical diagram 1800 illustrating the chemical structures and synthesis pathways of hydrogel F127-UDM (also referenced herein as F127-BUM), F127-UDA, and F127-UUDM.

When F-127-DMA is dissolved in an aqueous medium at a concentration of 20-35 wt %, a hydrogel is formed. This hydrogel is reversibly temperature responsive, wherein the material undergoes a gel-to-sol transition as it is cooled from room temperature to 5-15° C. This feature of the hydrogel facilitates the homogeneous incorporation of monomers, polymers, biopolymers, nanomaterials, and living cells within the liquid form of the hydrogel. When the liquid is warmed to room temperature, the hydrogel (or composite hydrogel) is formed. The hydrogel is also shear-thinning, which is important for the hydrogel to be extruded from the nozzle.

This hydrogel ink is highly versatile, as different additives can be included to modify the properties of the resulting hydrogel. For example, we examined the addition of varying amounts of poly(ethylene glycol) diacrylate to the hydrogel, in order to increase the overall storage modulus as a result of increased cross-linking density. Adding PEG-DA does not significantly change the storage modulus prior to UV irradiation. However, after UV irradiation, the storage modulus increases with the concentration of PEG-DA. The storage modulus increased more than 5-fold for the hydrogel with the highest concentration of PEG-DA tested compared to pure F127-DMA. Additionally, the rate of polymerization also correlated to the concentration of PEG-DA. F127-DMA without PEG-DA saw a gradual increase in modulus after UV initiation, requiring 61 seconds to reach its peak storage modulus. In contrast, the storage modulus of F127-DMA with 20 wt % PEG-DA began to plateau after only 12 seconds. The higher concentrations of PEG-DA increased both the storage modulus after UV curing as well as the rate of polymerization.

All gels exhibit linearly decreasing viscosity with increased shear rate, indicating shear thinning behavior. This shear thinning behavior is desirable for extrusion printing because the ink endures high pressure as it is forced through the small diameter nozzle. As the concentration of PEG-DA increases, the viscosity decreases. For example, hydrogel F127-DMA with 16 wt % PEG-DA has a lower viscosity than 12 wt % PEG-DA but higher than 20 wt % PEG-DA, which further supports this trend. FIG. 19 is a graph illustrating the rheological properties of F127-UDM, specifically shear-thinning behavior, showing a decreasing viscosity curve 1902 as a function of shear rate.

Hydrogels composed of PLURONIC® F127 (poloxamer 407) have temperature- and shear-responsive properties but lack the means of chemical cross-linking to afford robust rigid structures after 3D printing. The synthesis of F127 urethane dimethacrylate (F127-UDM) and F127 urethane urea dimethacrylate (F127-UUDM), (synthesis pathways shown in FIG. 18) enables light-responsive functionality while maintaining temperature and shear responses.

The polymers F127-UDM and F127-UUDM were synthesized as shown in FIG. 18. F127-UDM proceeded via a one-step tin catalyzed isocyanate reaction (reaction 1802) that required 2 days to reach 84% functionalization. Hydrogels made from this composition perform similar to F127-DMA hydrogels indicating them to be an ideal alternative material for 3D printing. F127-UUDM required a two-step process which involved the one-pot approach of CDI activation followed by the addition of ethylene diamine (reactions 1804) to generate an amine chain end referred to as F127 urethane diamine (F127-UDA). F127-UDA can be further functionalized using the same isocyanate in the absence of catalyst in an overnight reaction (reaction 1806) to yield F127-UUDM with 90% functionalization. This hydrogel appears to have higher stiffness and viscosity than F127-DMA and F127-UDM which suggests that the addition of a urea unit in the polymer affords some hydrogen-bonded self-assemblies.

Hydrogel Characterization

Phase diagrams based on polymer concentration and solution temperature were constructed to summarize the physical properties of the polymer solutions at temperatures ranging from 5 to 50° C. and polymer concentrations between 2 and 35 wt %. The vial inversion method was used to ascertain whether each sample was a liquid viscous liquid, or a gel. F127-UDM and F127-UUDM perform as homogenous hydrogels that undergo gel-to-sol transitions. Both polymers in water remained as a clear solution from 5 to 50° C. at 2 to 15 wt % and would not gel until 25° C. at 20 wt %. At 25 wt %, the mixtures had a slow transition from a clear solution at 5° C. to a viscous liquid until it gelled at 20° C. suggesting that this composition was ideal for 3D printing applications.

These hydrogels were further characterized by rheometry. The gel yield stress also provides an indirect indication of the gel strength as it supports subsequent stacked layers during 3D printing. In other words, a gel with a higher yield stress can support more stacked layers without printing defects such as sagging than a gel with a low yield stress. Hydrogels of F127-UDM and F127-UUDM have a yield stress of 640 Pa and 1230 Pa at 25 wt %, respectively. These results suggest that F127-UUDM is a stronger hydrogel, but it is also more difficult to extrude. Additionally, an ideal material for extrusion through a small diameter nozzle in extrusion-based-3D-printing is a shear-thinning polymer ink. All polymer hydrogels disclosed herein have linearly decreasing shear viscosities as the shear rate increases (see, e.g., FIG. 19) which is related to the pressure required to extrude in pneumatic based printing. The viscosity versus shear rates are similar between F127-DMA and F127-UDM but are higher at all shear rates for F127-UUDM. These results indicate the gels are non-Newtonian fluids that shear-thin. Therefore, these hydrogels are suitable for extrusion through the co-axial nozzles.

Fabrication and Experimental Validation of Large-Bore Hydrogel Tubes

For the validation of the bell-shaped nozzle for fabrication of large sized tubular constructs, a printhead assembly with the bell-shaped nozzle was used, and the single annular conduit of the nozzle was fed by a single syringe with manual pressure regulation. The hydrogel used was 30 wt % PLURONIC® F127 dimethacrylate with an addition of 97% 2-Hydroxy-2-methylpropiophenone (1.5 µL/g of hydrogel) (Sigma-Aldrich). The gel was prepared with deionized water and kept at ~6° C. and vortexed periodically until complete dissolution of the polymer was observed. 2-Hydroxy-2-methylpropiophenone was added two hours before extrusion at ~6° C.; the gel was then manually mixed and vortexed. Extrusion took place vertically into a light paraffin oil bath (Fisher Chemical).

Extrusion pressure was adjusted using a manual pressure regulator until a satisfactory extrusion rate was achieved, then the bath was raised toward the printhead assembly using a laboratory jack such that extrusion began taking place directly into the bath. Once a tube of desired length was produced, the tube-in-bath was immediately placed on a reflective aluminum surface under a dual-bulb (365 nm, 600 m W) UV lamp and was exposed to UV radiation for 20 minutes for photo-crosslinking of the hydrogel. After photo-crosslinking, the tube was removed from the paraffin oil bath and washed for five minutes in technical grade isopropyl alcohol to remove residual paraffin.

Fabrication and Experimental Validation of Small-Bore Hydrogel Tubes

According to various embodiments, extrusion of tubular hydrogel structures utilizing the concentric nozzle design is based on the co-extrusion of an outer cross-linkable hydrogel and an inner support hydrogel onto a flat surface or onto a gel bed similar or identical in composition to the inner support gel. (Referred to herein as coaxial, supportive inner hydrogel filament) The inner and/or outer hydrogel layers can be cross-linkable. The procedures which utilize the bell-shaped nozzle designs are based on the extrusion of a cross-linkable hydrogel into air, or into a support fluid bath. The latter method has notable limitations in the way of possible geometries that can be produced, as well as overall quality of extruded features; however, it enables fabrication of sizeable (centimeter-scale diameter) tubes without consumption of large volumes of support hydrogel. In both cases, nozzles can be attached to pneumatic syringes to produce a printhead assembly which can then be loaded onto a 3D printer carriage or stabilized in some other manner for stationary extrusion.

The procedures for the loading of hydrogel solution prior to extrusion, and the preparation of the printhead assembly, are similar for both coaxial and bell-nozzle methods described above. Prior to extrusion, hydrogels were cooled to about 6° C. and loaded into capped pneumatic syringe barrels (Nordson EFD). Cartridge pistons (Nordson EFD) were then inserted. Once at ~20° C., the loaded syringe barrels were uncapped and attached via Luer-lock fitting to the fabricated nozzle. The syringe-nozzle printhead assembly was then clamped to a laboratory ring-stand for stabilization. After stabilization of the syringe-nozzle printhead assembly, pneumatic syringe barrel adaptors (Nordson EFD) were installed on each syringe. Cartridge pistons were driven by low pressure (e.g. 50-125 kPa, 8-18 psi) nitrogen gas which was flowed through pressure regulators and/or valves, clear PVC tubing, and into the pneumatic syringe barrels via the syringe barrel adaptors.

For the fabrication of small-medium sized tubular constructs, a printhead assembly with the concentric nozzle was used. The inner and outer conduits of the nozzle were fed by separate syringes with independent pressure regulation. The hydrogel used in the syringe feeding the inner conduit was 30 wt % PLURONIC® F127 (Sigma-Aldrich) which was dyed purple with food coloring (Betty Crocker) for visibility. The hydrogel used in the syringe feeding the outer conduit was 30 wt % PLURONIC® F127 dimethacrylate with an addition of 97% 2-Hydroxy-2-methylpropiophenone (1.5 µL/g of hydrogel) (Sigma-Aldrich). Both gels were prepared with deionized water, and kept at ~6° C. and vortexed periodically until complete dissolution of the polymer was observed. 2-Hydroxy-2-methylpropiophenone was added two hours before extrusion at 6° C.; the gel was then manually mixed and vortexed.

Coextrusion took place onto a transparent polycarbonate sheet (Lexan). In some cases, the sheet was left bare, in other cases a thin layer of hydrogel, identical in composition to the inner hydrogel, was spread across the surface of the sheet to create a gel bed. Extrusion pressures were adjusted using manual pressure regulators until complementary extrusion rates were achieved. This was confirmed visually by first extruding just the inner gel, then extruding just the outer gel, then extruding both gels simultaneously (coextrusion). Once satisfactory coextrusion was achieved, the polycarbonate sheet was translated manually at a fixed height of ~50 mm until tubes of desired length and linear geometry were produced. Immediately following extrusion, the polycarbonate sheet was placed on a reflective aluminum surface under a dual-bulb (365 nm, 600 mW) UV lamp and tubes were exposed to UV radiation for 20 minutes for photo-crosslinking of the outer hydrogel. After photo-crosslinking, tubes were submerged in deionized water and kept at ~6° C. for a minimum of two hours, or until complete dissolution of the inner hydrogel, to yield a well-defined lumen, was observed.

Validation of Loading and Sealing Tubular Constructs

In order to examine the loading of gels into the lumens of tubular constructs, yeast-laden 23 wt % PLURONIC® F127 (Sigma-Aldrich) hydrogel was prepared with a liquid culture of wild-type S. cerevisiae and synthetic complete medium by mixing together PLURONIC® F127 and synthetic complete medium, then micro-pipetting in ~$10^7$ individuals per milliliter of gel. The mixture was kept at ~6° C. and vortexed periodically until complete dissolution of the polymer was observed. The yeast-laden hydrogel was dyed lime-green with food coloring (Betty Crocker) for visibility. 23 wt % gel was chosen for ease of manual injection; however, for the coextrusion method, yeast-laden 30 wt % PLURONIC® F127 prepared in an equivalent manner would have been suitable as well.

A pinch of yeast cells (S0992) were collected by a sterile wooden inoculation pick from a casted agar gel in YPD media. The cells were homogeneously mixed into 7 mL SC media and incubated at 30° C. under constant shaking at 225 rpm for 24 h. After this time, a thick precipitate was observed, indicating cell growth. Then, 100 µL of this solution was mixed with 1900 µL of SC media, and the optical density (OD) at 600 nm \Vas measured to approximate the number of cells (OD of 0.1 corresponds to $10^6$ cells/mL).

Injection of Cell Cultures or Organisms after Support Filament Removal

Loaded tubes were fabricated following the procedure previously discussed which utilizes the concentric nozzle design. Prior to extrusion, the concentric nozzle was washed in 70% ethanol and dried with pressurized nitrogen gas. For the post-fabrication-injection method, tubes were fabricated exactly as outlined initially with 30 wt % PLURONIC® F127 as an inner support hydrogel. After extrusion, photo-crosslinking, and removal of the inner support hydrogel via dissolution, a ~5 mm section from each tube end was removed with a sterilized razorblade to produce well-defined tube ends. One end of each tube was then sealed by manual deposition of hydrogel of identical composition to the outer crosslinkable hydrogel, through a 1 cc syringe (Norm-Ject) and 18-gauge needle (Metcal). The half-sealed tubes were then exposed to UV radiation for 10 minutes for photo-crosslinking of the seal. After curing of the single sealed ends, yeast-laden 23 wt % PLURONIC® F127 hydrogel was injected into each tube. Injection was carried out by first clamping a 1 cc syringe (Norm-Ject), loaded with yeast-laden hydrogel, vertically downward on a laboratory ring-stand, then attaching a 23-gauge needle (Metcal), then securing a tube onto a laboratory jack such that the lumen was in alignment with the syringe needle.

Once proper alignment was visually confirmed from two axes, the lab jack was carefully raised, resulting in the insertion of the needle into the tube lumen without contacting the walls of the lumen. After complete insertion, the syringe plunger was depressed, injecting the yeast-laden hydrogel. Following injection, the needle was withdrawn without contacting the lumen walls by carefully lowering the laboratory jack. The tube end was then sealed as described previously, and the loaded and sealed tube was photo-crosslinked for 20 minutes. After crosslinking, the sealed tube was washed ten times in a centrifuge tube with 45 mL of deionized water each time, for ~30 seconds per wash.

Coextrusion of Cell-Containing Hydrogel Media

Loaded tubes were fabricated following the procedure previously discussed which utilizes the concentric nozzle design. Prior to extrusion, the concentric nozzle was washed in 70%; ethanol and dried with pressurized nitrogen gas. Instead of the use of 30 wt % PLURONIC® F127 as an inner support hydrogel, yeast-laden 23 wt % PLURONIC® F127 hydrogel, to be used as a permanent filler, was loaded into the syringe feeding the inner conduit. After loaded tubes of desired length and linear geometry were extended in the manner previously discussed, a ~5 mm section from each tube end was removed with a sterilized razorblade to produce well-defined tube ends. The ends were then sealed by manual deposition of hydrogel of identical composition to the outer crosslinkable hydrogel, through a 1 cc syringe (Norm-Ject) and 18-gauge needle (Metcal). Loaded tubes were then photo-crosslinked for 20 minutes and then washed ten times in a centrifuge tube with 45 mL of deionized water each time, for ~30 seconds per wash.

Validation of Hydrogel Tubes with Luminal Cell Culture

Various embodiments disclosed herein for fabricating tubular structures involve material extrusion through dies with annular orifices. Standalone tubular structures can be used as vascular grafts,[19,20,24] nerve guidance conduits,[18,25,26] grafts for urethroplasty,[27-29] and tracheal grafts,[30] among other applications. More complex, perfusable, cell-laden constructs which utilize tubes as a basic structural motif can be used to recapitulate tissue or organ function.[31-33]

Hydrogels are attractive materials for many biomedical applications due to their significant water content and mechanics reminiscent of soft tissues.[34,35] However, it remains challenging to reconcile biocompability, bioactivity, and mechanics in hydrogels with processability in the context of extrusion.[36] Previous reports have succeeded in outlining sets of biochemical and biophysical material properties which are essential for the recapitulation of many physiological functions,[37-39] yet the incorporation of these properties into materials used in extrusion-based fabrication processes remains a challenge.

Hydrogels that have thus far been processed into tubular structures for potential biomedical applications include those based on gelatin,[8,9] hyaluronic acid,[10] alginate,[12,13] collagen,[14,16] poly(vinyl alcohol),[17,20] silk fibroin,[18] fibrin,[19] and decellularized extracellular matrix.[21] Recently, Pi et al.[8] have demonstrated coaxial extrusion-based fabrication of circumferentially-layered tissue-engineered tubular constructs using materials based on methacrylated gelatin, alginate, and acrylated multi-arm poly(ethylene glycol). The authors produced these constructs using urothelial and vascular endothelial cells and smooth muscle cells. These tissue-engineered constructs represent an important step toward creating engineered replacements for tubular biological structures. However, this platform involves handmade extrusion hardware, which may restrict the platform's accessibility and customizability. 3D printing enables modular fabricate of coaxial nozzles without additional machining or expertise associated with manual production. As a result, smaller nozzle features with a precision directly correlated to the 3D printer are now possible.

Several embodiments disclosed herein relate to the use of coaxial nozzles in combination with extrudable hydrogels based on a derivative of PLURONIC® F127 hydrogel. The employment of 3D printing advantageously allows the rapid design, fabrication, and iteration of extrusion hardware possessing relatively complex geometries. The platforms outlined herein, including the materials and process-design principles highlighted, can broadly serve as an example of effective implementation of design for additive manufacturing in the context of biofabrication. A notable advantage of this platform stems from its broad accessibility, as the CAD files of the coaxial nozzles can be modified to meet a variety of needs, and the nozzles can be printed on commercially available desktop SLA 3D printers.

Materials for Validation of Hydrogel Tubes with Luminal Cell Culture

The following materials were used to validate the preparation of endothelial-cell containing hydrogel tubes, in accordance with various embodiments: PLURONIC® F127 (P2443-1 KG; referred to as F127), phenol red solution (P0290-100ML; 0.5%), sodium hydroxide solution (S2770-100ML; 1.0 M), 2-hydroxy-4'-(2-hydroxyethoxy)-2-methylpropiophenone (410896-10G; 98%; referred to as IRGACURE 2959), and 2-acrylamido-2-methyl-1-propanesulfonic acid sodium salt solution (655821-250ML; 50 wt %; referred to as AMPS) were all purchased from Sigma Aldrich, St. Louis, Mo., USA. Dibutyltin dilaurate (D0303; >95.0%) was purchased from TCI America, Portland, Oreg., USA. 2-Isocyanatoethyl methacrylate (ACT34296) was purchased from Arctom Chemicals, Newton, Mass., USA. $CDCl_3$ (DLM-7-PK; 99.8%) was purchased from Cambridge Isotope Laboratories, Tewksbury, Mass., USA. Common solvents (Certified ACS) and phosphate-buffered saline (PBS) tablets (BP2944100) were purchased from Fisher Scientific, Waltham, Mass., USA. Collagen I from rat tail tendon (354249; 8.3 mg/mL in 0.02 M acetic acid) was purchased from Corning, Inc., Corning, N.Y., USA. Ammonium hydroxide (AX1303; 28.0-30.0 wt %) was purchased from EMD Millipore. Autodesk Standard Clear Prototyping Resin (also known as PR48) was purchased from Colorado Photopolymer Solutions, Denver, Colo., USA. Formlabs, Inc., Somerville, Mass., USA Clear photopolymer resin (FLGPCL04) was purchased from Formlabs, Inc., Somerville, Mass., USA.

Human umbilical vein endothelial cells (C2517A; single donor; in EGM-2; referred to as HUVECs) and endothelial cell growth medium (CC-3162; referred to as EGM-2) were purchased from Lonza Inc., Hayward, CA, USA. Penicillin-streptomycin cocktail (Ser. No. 15/140,122; 10000 U/mL), ethidium homodimer-1 (E1169), calcein AM (C3100MP), and 4',6-diamidino-2-phenylindole (D1306; referred to as DAPI) were all purchased from Thermo Fisher Scientific, Waltham, MA, USA. Subculture Reagent Kit (090K; containing HMS, Trypsin/EDTA & Trypsin Neutralizing Solution) was purchased from Cell Applications Inc., San Diego, CA, USA. Paraformaldehyde solution (50-980-487; 16%), bovine serum albumin (BP9706100; referred to as BSA), polysorbate 80 (AC278632500; referred to as P80), and Alexa Fluor 488-goat anti-mouse IgG (NC0675427; IgG polyclonal; H+L) were all purchased from Fisher Scientific, Waltham, MA, USA. Triton X-100 (X100-100ML) was purchased from Sigma Aldrich, St. Louis, MO, USA. Mouse anti-human CD31 (MCA1738; IgG1 monoclonal; clone WM59) was purchased from Bio-Rad Laboratories Inc., Hercules, CA, USA. All reagents were used as received unless otherwise specified.

Instrumentation for Validation of Hydrogel Tubes with Luminal Cell Culture

The $^1H$ NMR spectrum was obtained using a Bruker AVANCE series instrument with 500 MHz frequency (Bruker Daltronics Inc., Fremont, CA, USA). Gel permeation chromatography (GPC) was performed using a Waters Breeze 2 chromatograph equipped with two 10 μm Malvern columns (300 mm×7.8 mm) connected in series with increasing pore size (1000, 10000 Å), using chloroform as the eluent, and calibrated with poly(ethylene glycol) standards (102 to 40000 g/mol) (Waters Corp., Milford, MA, USA). Rheometric experiments were performed using a TA Instruments Discovery Hybrid Rheometer-2 (DHR-2) equipped with an Advanced Peltier Plate system for temperature control, and a 365 nm LED UV-curing accessory with disposable acrylic plates for photorheology experiments (TA Instruments Inc., New Castle, DE, USA). All rheometric experiments were performed using a stainless steel 20 mm upper plate. Coaxial nozzles were 3D printed using an Autodesk Ember DLP 3D Printer or a Formlabs Form 2 SLA 3D Printer. Fluorescence microscopy was performed on a Zeiss Axiovert 200 with Axiocam 503 mono camera (Carl Zeiss, Inc., Dublin, CA, USA). Confocal microscopy was performed on a custom-built simultaneous 4-channel Nikon AR1 with cMOS camera with xyz-motorization (Nikon Instruments Inc., Melville, NY, USA).

Synthesis of F127-UDM

The synthesis of F127-bisurethane methacrylate (F127-UDM, or alternatively F127-BUM) can be described as follows. Briefly, F127 (60 g, 4.8 mmol) was dried under vacuum, and anhydrous $CH_2Cl_2$ (550 mL) was charged to the flask. The mixture was stirred until complete dissolution of the F127 was observed. Dibutyltin dilaurate was then added, and the 2-isocyanatoethyl methacrylate (3.5 mL, 24.8 mmol) was diluted in anhydrous $CH_2Cl_2$ (50 mL) and added dropwise to the reaction mixture. The reaction was allowed to proceed for 2 d before being quenched by the addition of MeOH. The F127-UDM was precipitated in $Et_2O$ before separation via centrifugation. The F127-UDM precipitate was finally washed in $Et_2O$, prior to being dried under vacuum.

Preparation of F127-UDM Hydrogel with Collagen I Additive

Collagen I (1.2 mL; 8.3 mg/mL in 0.02 M acetic acid) was added to chilled, sterilized $dH_2O$ (2.21 mL). The mixture was swirled thoroughly before the addition of F127-UDM (1.5 g). Immediately after addition of the F127-UDM, the mixture was vortex-mixed and placed on ice for approximately 3 h until dissolution of the F127-UDM was observed. A 5 wt % solution of IRGACURE 2959 was prepared by adding sterilized dH$_2$O to IRGACURE 2959 and incubating for 30 min at 70° C. before briefly vortex-mixing. After dissolution of the F127-UDM, the IRGACURE 2959 solution (100 µL; 5 wt %) was added to the gel, and the gel was vortex-mixed again briefly. The gel was kept on ice overnight and vortex-mixed the following day, followed by centrifugation at approximately 600 g for 1 min. This process was repeated two to three times until a homogeneous, slightly turbid gel was observed. The gel was kept on ice whenever possible during this time. The gel was stored in the dark at 4° C. and used within 3 d. Prior to use, bubbles (if remaining) were eliminated by brief centrifugation at approximately 600 g.

Preparation of F127-UDM Hydrogel with AMPS Additive

AMPS solution (1.0 g; 50 wt %) was added to chilled, sterilized dH$_2$O (2.4 mL). The mixture was swirled briefly before the addition of F127-UDM (1.5 g). Immediately after addition of the F127-UDM, the mixture was vortex-mixed and placed on ice for approximately 3 h until dissolution of the F127-UDM was observed. IRGACURE 2959 solution (100 µL; 5 wt %) was then added to the gel, and the gel was vortex-mixed again briefly. The 5 wt % solution of IRGACURE 2959 was prepared as described previously. The gel was also stored and conditioned as described previously.

Preparation of F127-UDM Hydrogel without Additive

F127-UDM (1.5 g) was added to chilled, sterilized dH$_2$O (3.4 mL). Immediately after addition of the F127-UDM, the mixture was vortex-mixed and placed on ice for approximately 3 h until dissolution of the F127-UDM was observed. IRGACURE 2959 solution (100 µL; 5 wt %) was then added to the gel, and the gel was vortex-mixed again briefly. The 5 wt % solution of IRGACURE 2959 was prepared as described previously. The gel was also stored and conditioned as described previously.

Preparation of Sacrificial F127 Core Hydrogel

Unfunctionalized F127 (1.5 g) was added to chilled, sterilized dH$_2$O (3.5 mL). Immediately after addition of the F127, the mixture was vortex-mixed and phenol red solution (150 µL; 0.5 wt %) was added. NaOH (10 µL; 1.0 M) was also added to bring the gel to approximately pH 7.4. The gel was vortex-mixed again briefly and placed on ice for approximately 3 h until dissolution of the F127 was observed. The gel was stored and conditioned as described previously.

Coaxial Nozzle Fabrication for Validation of Hydrogel Tubes with Luminal Cell Culture According to various embodiments of the present disclosure, coaxial nozzles were printed using an Autodesk Ember DLP 3D Printer with the Autodesk Standard Clear Prototyping Resin, also known as PR48 (Colorado Photopolymer Solutions, Denver, CO, USA) or a Formlabs Form 2 SLA 3D Printer with Formlabs Clear photopolymer resin (Formlabs, Inc., Somerville, MA, USA). In all cases, 50 µm was selected as the layer height. The standoff from the build surface was set to 0 mm, and nozzles were printed such that their superior surfaces made contact with the build surface. Support structures were not used. Following completion of prints, nozzles were rinsed with isopropanol. The nozzles were then purged and dried with pressurized air and post-cured according to the manufacturer's instructions. Following 3D printing and completion of the post-printing steps described, 14 gauge×0.5 in straight and bent (45°) blunt-tip needles (OK International) were affixed to the superior and lateral inlets, respectively, of each coaxial nozzle. The straight needle was ground short and deburred such that the remaining length of the cannula was roughly 5 mm. This measure was taken to reduce the overall height of the fully-assembled coaxial nozzle and is not a necessary step. Alternatively, 14 gauge×0.25 in needles could be used. Loctite 495 cyanoacrylate adhesive was used to affix the needles. Following assembly, each nozzle was washed with 70% isopropanol and stored at room temperature in dH$_2$O until further use. Prior to use, nozzles were rinsed briefly with 70% EtOH.

Fabrication of Hydrogel Tubes for Validation of Hydrogel Tubes with Luminal Cell Culture Unless otherwise specified, tubes were fabricated using coaxial nozzle methods with a 2 mm outer conduit diameter. Gels chilled on ice were loaded into syringes (Nordson EFD), and once the gels reached room temperature, an extrusion setup similar to that shown in FIG. 1 was assembled. The syringe containing the sacrificial (inner) hydrogel was affixed to the apical inlet and the syringe containing the outer hydrogel was affixed to the lateral inlet of the coaxial nozzle. Syringe barrel adapters (Nordson EFD) were then attached to each syringe. Pressure to drive the syringe pistons was supplied by an in-house N2 line. The pressure was controlled independently for each syringe around 55-100 kPa, nominally, by 0-210 kPa pressure regulators and gauges. To adjust pressures prior to extrusion, the tubing of each syringe barrel adapter was clamped using a pinch-clamp, and the regulators were set to the desired pressures. To begin extrusion, the tubing of each adapter was unclamped, and after waiting a moment for the coaxial extrusion rate to stabilize, a 4 in×6 in glass sheet was manually translated under the nozzle to catch the coaxial gel filament. The shell of the coaxial filament (outer gel) was then photo cross-linked for 20 min under a UV lamp (365 nm, 3.3 mW/cm$^2$). The sacrificial core of the coaxial filament (inner hydrogel filament) was removed via dissolution in aqueous medium to yield the hydrogel tube. 1×PBS was used as the dissolution medium for hydrogel tubes used in cell seeding experiments; dH$_2$O was used for hydrogel tubes for all other purposes.

Cell Seeding for Validation of Hydrogel Tubes with Luminal Cell Culture

An F127-UDM hydrogel with collagen I additive was used in the fabrication of tubes and discs for cell seeding experiments. The F127-UDM hydrogel without collagen I additive was used in the fabrication of discs as a negative control. HUVECs were maintained in endothelial cell growth medium (EGM-2 supplemented with 100 units/mL penicillin and 100 ng/mL streptomycin). Cells were maintained in a 37° C. incubator with 5% CO2. Cells of passage number 4-8 were used for all cell seeding experiments.

Fabrication of Hydrogel Discs and Preparation for Cell Seeding Experiments

Fabrication of hydrogel discs and preparation for cell seeding is described below. Briefly, a pair cured hydrogel sheets were prepared from F127-UDM hydrogels with and without collagen I additive. The sheets were placed in 1×PBS and incubated at 37° C. for 1 h. A biopsy punch (5 mm) was then used to punch gel discs from the sheets. Discs were sequentially washed with dH$_2$O, 70% EtOH, and sterilized 1×PBS. Discs made from F127-UDM hydrogel with collagen I additive were dehydrated in an incubator at 37° C. The discs without collagen (negative control) were transferred to endothelial cell growth medium and stored at 4° C. in medium until cell seeding. Following dehydration, F127-UDM discs with collagen I were subjected to a dehydration/rehydration procedure as described in section 2.7.1: discs were submerged in collagen I solution and were allowed to rehydrate. Following rehydration, discs were briefly exposed to ammonia vapor. Discs were then once again placed in a 37° C. incubator to dehydrate. The rehydration procedure was repeated once more, and following another dehydration, a similar rehydration procedure was carried out with endothelial cell growth medium instead of collagen solution. Following a final dehydration, discs were rehydrated with the growth medium and stored in medium at 4° C. until cell seeding.

Preparation of Hydrogel Tubes for Cell Seeding

Preparation of hydrogel tubes for cell seeding is described below. Briefly, following coaxial extrusion and photo-cross-linking as described previously (with the F127-UDM hydrogel with collagen I additive used as the shell), the coaxial filament was placed in 1×PBS and incubated at 37° C. for 1 h to facilitate dissolution of the sacrificial core hydrogel. The resulting tube was sectioned (~20 mm long sections), and the tube sections were sequentially washed with dH$_2$O, 70% EtOH, and sterilized 1×PBS. The tube sections were then dehydrated in an incubator at 37° C. Following dehydration, tube sections were submerged in collagen solution (6.0 mg/mL in 0.014 M acetic acid) and were allowed to rehydrate. Following rehydration, tube sections were briefly exposed to ammonia vapor to facilitate pH- and temperature-dependent cross-linking of the collagen. Tube sections were then once again placed in a 37° C. incubator to dehydrate. The rehydration procedure was repeated once more, and following another dehydration, a similar rehydration procedure was carried out with endothelial cell growth medium instead of collagen solution. Following a final dehydration, tube sections were rehydrated with the growth medium and stored in medium at 4° C. until cell seeding.

Figure 20A:
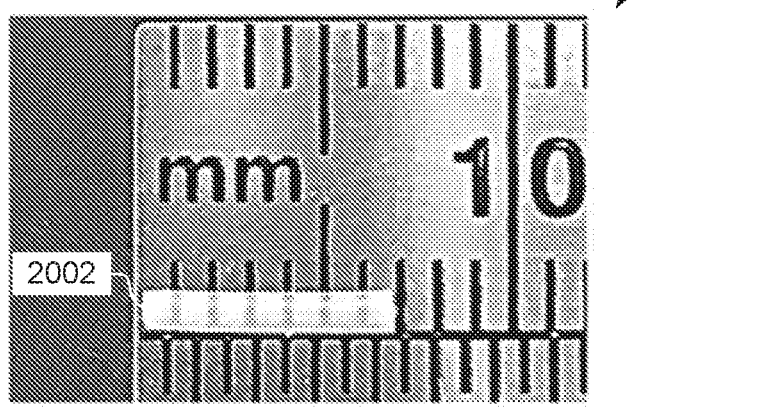
FIGS. 20A and 20B are a pair of images of dehydrated and rehydrated hydrogel tubes.
Figure 20B:
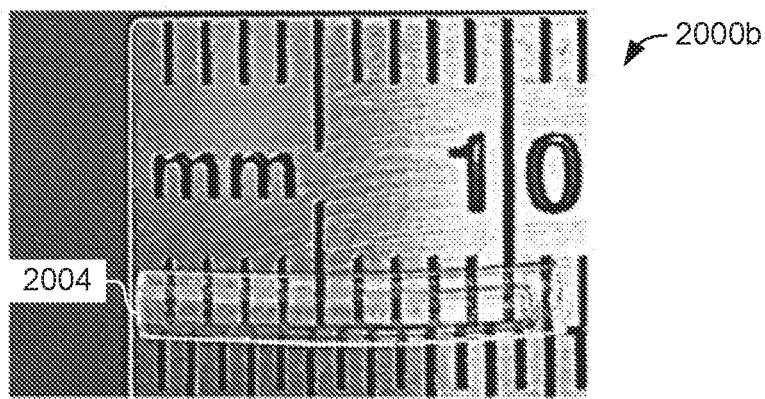

Tube sections can readily withstand dehydration and rehydration, as shown in FIGS. 20A and 20B. FIG. 20A is a first image 2000a showing a dehydrated tube section 2002, and FIG. 20B is a second image 2000b showing the same, rehydrated tube section 2004. Although the process of dehydration and rehydration temporarily deforms the hydrogel tubes, as shown in FIG. 20B, the hydrogel tubes revert to their previous clarity, flexibility, and dimensions following rehydration.

HUVEC Seeding and Culture on Discs

Briefly, cell suspension was pipetted directly onto each disc and additional growth medium was added around each disc. Cells were incubated at 37° C. and 5% CO2. Medium was replaced every 24 h. Viability was evaluated at 24, 48, and 72 h via staining with calcein AM and ethidium homodimer-1. For visualization of cell morphology via DAPI staining and indirect immunofluorescence, discs were removed from the medium after 48 h. Cells were fixed in 4% paraformaldehyde prior to staining and immunocytochemical treatment.

HUVEC Seeding and Culture in Tube Sections

For cell seeding in tube sections, HUVECs were trypsinized and resuspended at a concentration of approximately $1.0 \times 10^6$ cells/mL in EGM-2 with penicillin-streptomycin. Sterilized blunt-tip needles (14 gauge×0.5 in) were attached to 1 mL syringes, and a tube section was gently slipped onto each needle. Tube sections were briefly rinsed by drawing growth medium into, and through, the lumens. Approximately 100 µL of the cell suspension was then drawn through the tube sections so that lumens were filled with cell suspension. Tube sections with syringes attached were transferred to a poly(styrene) BioAssay dish lined with Kimwipes soaked in 1×PBS. The tube sections and syringes were kept horizontally in the BioAssay dish during a 1 h incubation at 37° C. and 5% CO2. Throughout the incubation, tube sections and attached syringes were rotated 90° every 15 min to ensure uniform access of cells to luminal walls. While in the dish, syringes were kept from rolling using 3D printed poly(lactic acid) syringe stands (FlashForge Creator Pro). Following the 1 h incubation, tube sections were removed from syringes and transferred to growth medium in a 6-well poly(styrene) culture plate (2 mL of medium per tube section; two tube sections per well) and additionally incubated for up to 72 h at 37° C. and 5% CO2. Medium was replaced after 48 h in culture. Prior to visualization of cell morphology in tube sections via DAPI staining and indirect immunofluorescence, tube sections were removed from the medium, transferred to a new culture plate, and briefly rinsed with 1×PBS. Cells were fixed at room temperature in 4% paraformaldehyde for 20 min. For rinses and fixation, a 1 mL syringe with a blunt-tip needle was briefly used to draw solution into the lumen of each tube section; each tube section was then immediately slipped off of the syringe needle and into a well of a 6-well poly(styrene) culture plate containing enough solution to submerge the tube section.

Staining and Immunocytochemistry

Following fixation, tube sections or discs were rinsed with 1×PBS and then sequentially treated with permeabilization buffer, blocking buffer, and primary antibody. Samples were then allowed to sit overnight. After removal of the primary antibody, samples were washed with washing buffer, and then treated with secondary antibody. After removal of the secondary antibody, samples were washed with washing buffer and then treated with DAPI in 1×PBS. Following brief incubation with DAPI, samples were washed with washing buffer and imaged via confocal microscopy.

Experimental Fabrication of 3D Printed Nozzles for Hydrogel Extrusion

We employed commercially available SLA 3D printers to fabricate coaxial nozzles with intricate, sub-millimeter cross-sectional features and hollow internal geometries. Our basic coaxial nozzle design consisted of a tubular inner conduit supplied by a superior inlet and an annular outer conduit supplied by a lateral inlet.

The close tolerances of luer lock connectors, as well as the relative brittleness of many cured photopolymer resins, precluded the reliable 3D printing of functional integrated luer lock connectors on the nozzles, using our 3D printers. Therefore, once the nozzles were printed, blunt-tip 14-gauge needles were affixed to the nozzle inlets to provide a means of attachment of syringes via a luer lock connection.

In order to provide a large contact area between the printer's build surface and the nozzles, and thus reduce the risk of the nozzles detaching during printing, we included a large superior surface on the nozzles. The nozzles were also designed to be 3D printed without the need for substantial pre-print or post-print processing—e.g., without utilizing support structures. Additionally, strength and rigidity of the nozzles were prioritized in order to resist elastic deformation-induced loss of coaxiality during extrusion and also to resist breakage during use and handling. This consideration entailed, in part, inclusion of thick, tapered walls and placement of the lateral inlet virtually flush with the superior inner surface (i.e., ceiling) of the nozzle. Finally, to ensure widespread practicability of this platform, we implemented a modular design; rapid iteration and customization of nozzle models is afforded simply by editing the dimensional constraints of the template CAD files. The fully assembled nozzles were used in combination with commercially available pneumatic syringes and adapters for extrusion of shear-thinning hydrogels.

Experimental Fabrication of Hydrogel Tubes for Seeding with Endothelial Cells

Shear-thinning hydrogels as described herein for extrusion-based processes readily flow through the nozzles during dispensation but then rapidly regain their gel character upon exiting, enabling maintenance of the extruded form. A material's reversible response to shear load and the time dependence of the response are used when evaluating a material's suitability for extrusion.[44,45]

In order to ensure fidelity of tubes' cross-sectional profiles to those of the nozzles, we employed two types of hydrogels during the coaxial extrusion process: non-cross-linkable and cross-linkable. A non-cross-linkable hydrogel was formulated from a commercially available amphiphilic triblock copolymer, F127 and was used as a sacrificial core material. A cross-linkable hydrogel was formulated from a derivative of F127, namely, F127-UDM and was employed for the tube walls. IRGACURE 2959 was added to cross-linkable F127-UDM-based hydrogels as a photoradical generator.

The F127-UDM was synthesized via reaction of F127 with 2-isocyanatoethyl methacrylate. While there are numerous reports featuring F127 functionalized with (meth) acrylate groups, we found that this particular reaction afforded excellent conversion and facile removal of byproducts. The F127-UDM-based hydrogels retained the rheological characteristics typical of hydrogels of F127. Namely, the hydrogels exhibited shear-thinning behavior as evidenced by their decreasing apparent viscosities with increasing shear rates, and the rapid recovery of their storage moduli during cyclic shear strain experiments.

In addition to their shear-thinning behavior, hydrogels based on F127 or F127-UDM also exhibited a temperature dependent reversible sol-gel transition, which is driven by a lower critical solution temperature (LCST) response of the polymer.

The gelation temperatures ($T_g$ei) for the F127-UDM-based hydrogels were determined by the cross-over point between the loss and storage moduli in each temperature ramp experiment. For the F127-UDM hydrogel without additive, $T_{gel} \approx 13.7°$ C.; for the hydrogel with collagen I additive, $T_{gel} \leq 13.6°$ C.; for the hydrogel with AMPS additive, $T_{gel}$ was depressed below 5° C.; however, cooling this gel in an ice bath was sufficient to induce the gel-to-sol transition.

The thermo-responsive behavior of the F127- and F127-UDM-based hydrogels facilitated formulation and processing of these materials. After the gel-to-sol transition was induced for each hydrogel composition, it was possible to transfer these materials into pneumatic syringes without difficulty. The materials were then allowed to return to room temperature, at which point they regained their gel states and were ready for extrusion.

Coaxial filaments containing a sacrificial core (29 wt % F127 hydrogel) and a cross-linkable shell (30 wt % F127-UDM hydrogels with or without additives and with photoradical generator) were extruded using the 3D printed coaxial nozzles. The extruded coaxial filaments were cured with UV light (365 nm) to initiate polymerization of the methacrylate groups and cross-link the outer hydrogel. The coaxial filaments were then rinsed with excess water or PBS to dissolve the uncross-linked sacrificial core hydrogel, yielding a tube.

For purposes of fabricating standalone tubes from F127-UDM-based hydrogels, it is generally not necessary to extrude a sacrificial core hydrogel, but in the event that other hydrogel compositions are utilized, an F127-based core hydrogel may be used to prevent distortion or collapse of the tube before curing. Furthermore, the core hydrogel was dyed with phenol red to aid in visualization of the lumen size during extrusion, which is convenient if extrusion pressures are not predetermined and are manually adjusted.

In order to demonstrate the versatility of this approach for fabricating tubes of a range of sizes, we employed three different coaxial nozzle sizes. The largest nozzle in this work consisted of an overall orifice diameter (corresponding to the extruded tube outer diameter) of approximately 2 mm. The smallest-size nozzle consisted of an overall orifice diameter of approximately 0.5 mm. Following fabrication, these small-diameter tubes were submerged in deionized water and perfused with a dye solution to demonstrate patency.

When cured, 30 wt % hydrogels based on F127-UDM are relatively tough and elastic, can be tied, or can be distended by addition of water.

Luminal diameters and wall thicknesses were determined by the dimensions of the nozzle, as well as the core and shell extrusion pressures. We found that in cases where inner and outer extrusion pressures were well matched, higher fidelity to nozzle dimensions was observed, and overall extrusion rate was adjusted by increasing or decreasing the extrusion pressures in tandem. In cases where the shell extrusion pressure was higher than the core extrusion pressure, the overall extrusion rate (i.e., length of coaxial filament generated per unit time) was limited by the core extrusion rate due to adhesion between the two hydrogels. In these situations, the shell hydrogel exhibited a volumetric flow rate mismatched with the overall extrusion rate, which yielded a tube with a relatively small luminal diameter and a thick wall. In cases where the core extrusion pressure was higher than the shell extrusion pressure, the reverse situation occurred—i.e., a tube with a relatively large luminal diameter and a thin wall was produced. In these cases of extrusion pressure mismatch, overall extrusion rate could still be varied while keeping the coaxial filament geometry approximately constant by adjusting the mismatched pressures in tandem.

The luminal diameters and outer diameters of extruded tubes were found to be generally consistent along the lengths of the tubes. The variations in these dimensions of two different F127-UDM tubes produced using the same (medium-size; 1.25 mm outer conduit diameter) nozzle with different sets of extrusion pressures were evaluated at five different points (approximately 10 mm apart) along the length of each tube. For the tube with the smaller lumen, the luminal diameter averaged 0.20±0.01 mm, and the outer diameter averaged 0.74±0.01 mm. For the larger-lumen tube, luminal diameter averaged 0.43±0.01 mm, and the overall diameter averaged 0.70±0.01 mm.

Extruded tubes or coaxial filaments with more complex cross-sectional profiles may also be fabricated as seen in FIGS. 15A and 15B. A "tube" with a 5-point star cross-sectional geometry was generated analogously to other tubes using a coaxial nozzle with a star geometry at its end. This demonstrated that more complex orifice geometries could be modeled at the ends of these nozzles; changing the overall nozzle structure or internal geometry was not necessary.

F127-UDM-based hydrogels can be derivatized with other chemical functionalities via co-polymerization with aqueous-soluble (meth)acrylate monomers. While this approach for introducing chemical species into the hydrogel network has been demonstrated for a range of monomers,[45] here we examined the incorporation of 2-acrylamido-2- methyl-1-propanesulfonic acid sodium salt (AMPS) to alter the swelling behavior of the extruded hydrogel tube. A hydrogel formulation with 30 wt % F127-UDM and 10 wt % AMPS was prepared, and its rheological behaviors were evaluated. Following fabrication, tubes with and without the AMPS additive were allowed to swell to equilibrium in deionized water. The average water mass fraction of the tubes with AMPS (n=4) was 92.3±0.3% and the average water mass fraction of the tube without AMPS (n=4) was 82.9±1.3%.

Visualization of Hydrogel Substrates and Hydrogel Tubes Seeded with Endothelial Cells Endothelial cells, which line the luminal surfaces of blood vessels, are one of the principal cellular components of the vascular system, wherein, in addition to fulfilling a variety of other roles, they make up the vascular barrier (endothelium) and control the extravasation of blood proteins and cells. Typical two-dimensional cultures of vascular endothelial cells on glass or poly(styrene) cell cultureware do not recapitulate physiology related to 3D geometry. Consequently, there is considerable interest in widely practicable platforms that enable more representative cultures of vascular endothelial cells.[47-49]

Prior to seeding HUVECs on the luminal surfaces of our hydrogel tubes, we first screened our materials for biocompatibility and cell-adhesion by producing small (~5 mm) cross-linked hydrogel discs with identical hydrogel compositions and analogous preparation to our tubes. In preliminary experiments in which we seeded HUVECs on the surfaces of discs made from cross-linked F127-UDM hydrogel without additive, we stained the cells with calcein AM after 24 h in culture in order to visualize cell morphology and infer cell adhesion to the hydrogel surface. These initial results suggested that this material does not promote adhesion of HUVECs—i.e., when cells were seeded directly onto the surfaces of the hydrogel discs, cells retained a rounded morphology, indicating a lack of adhesion. The high poly(ethylene oxide) (PEO) content of F127 (~72-75%) affords a cross-linked material that resists protein adsorption and cell adhesion.[51-55]

Collagen I was used to promote cell adhesion to the F127-UDM surface. The thermo-responsive gelation behavior of F127-UDM facilitated the homogenous incorporation of soluble collagen into the hydrogel at low temperatures. Bulk concentrations of collagen I well in excess of 0.2 wt % in the F127-UDM (30 wt %) hydrogels led to substantial aggregation of collagen, causing visible inhomogeneity in the gel, which was detrimental to extrusion quality. The inclusion of collagen I as an additive at no more than 0.2 wt %, however, was not substantially detrimental to the desirable rheological characteristics of the hydrogel and afforded high-quality tubes.

The adhesion of HUVECs to the hydrogel surface improved substantially with the incorporation of collagen into the hydrogel formulation; however, we observed that the functionalization of F127-UDM hydrogel with collagen I was more effective when collagen was not only incorporated into the hydrogel formulation prior to fabrication of discs or tubes but also coated onto the cross-linked hydrogel surfaces post-fabrication. The latter was achieved via multiple rounds of rehydration of dehydrated hydrogel constructs (i.e., tubes and discs) in solutions of collagen I. After this process was established, HUVEC morphology and viability were again evaluated by fabricating hydrogel discs functionalized in this way and seeding the cells onto their surfaces. At 24 h in culture, we observed that cells had adhered to the disc surfaces, as evidenced by the spread morphology. Beyond cell adhesion, viability of cells cultured on collagen-treated discs made from the F127-UDM hydrogel with collagen I additive was found to be satisfactory after 72 h in culture.

To demonstrate the application of this platform toward the fabrication of models of vascular endothelium, we prepared tubes for the luminal-seeding and culture of HUVECs. Tubes were prepared with the F127-UDM hydrogel with collagen I additive and were treated with collagen I in a manner analogous to the discs discussed above (dehydration/rehydration). To characterize morphology of the HUVECs on the luminal surfaces of tubes, we visualized the interendothelial junction marker CD31 (also referred to as platelet endothelial cell adhesion molecule, PECAM-1) via indirect immunofluorescence after 72 h of culture. The expression and localization of CD31 indicates appropriate general endothelial phenotype.[56]

Figure 21A:
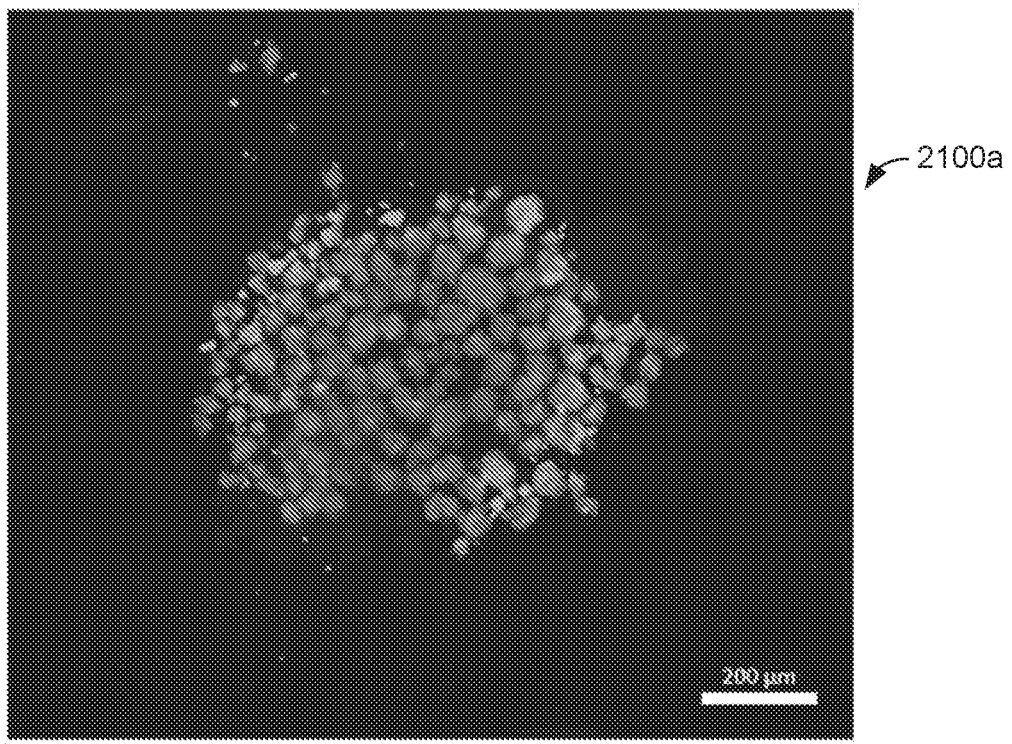
FIGS. 21A and 21B are a pair of fluorescent microscope images of collagen-impregnated hydrogel surfaces colonized by endothelial cells, with and without collagen-solution retreatment.
Figure 21B:
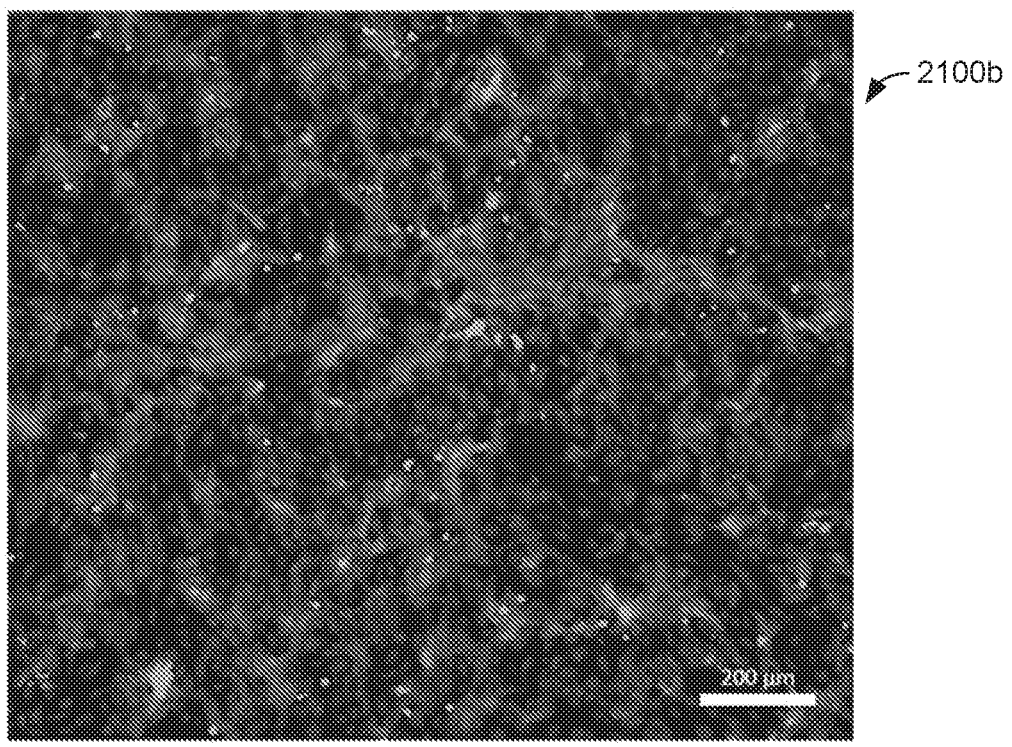

FIG. 21A and FIG. 21B are a pair of fluorescent microscope images of collagen-impregnated hydrogel surfaces colonized by endothelial cells, with and without collagen-solution retreatment. Specifically, FIG. 21A is a fluorescent confocal micrograph 2100a showing HUVECs seeded on cross-linked unmodified F127-UDM hydrogel (disc) after 24 h in culture.

Cells stained with calcein AM (green) for visualization show aggregation and rounded morphology, indicating lack of adhesion. FIG. 21B is a second fluorescent confocal micrograph 2100b showing HUVECs seeded on cross-linked, collagen I-treated F127-UDM hydrogel with collagen I additive (disc) after 24 h in culture. Cells stained with calcein AM for visualization show spreading, indicating adhesion. The difference between culture adhesion and viability between unmodified and collagen-impregnated hydrogel substrates is evident in the difference between endothelial cell spread between FIGS. 21A and 21B, with the collagen-impregnated substrate demonstrating significantly improved viability.

Figure 22A:
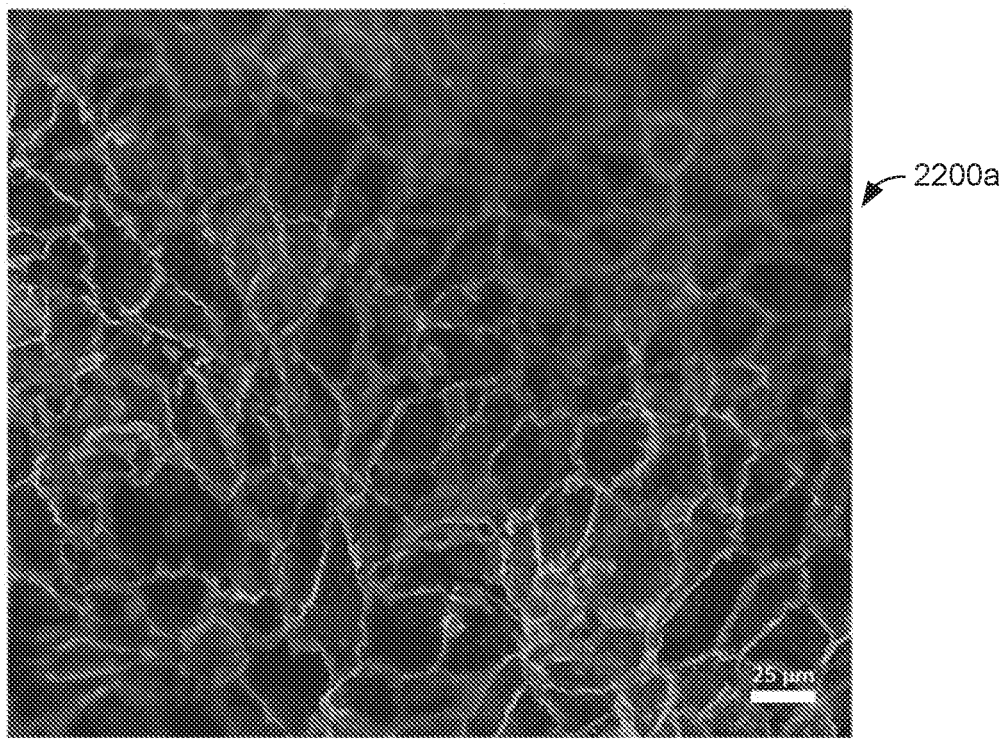
FIGS. 22A and 22B are a pair of fluorescent microscope images of collagen-impregnated hydrogel surfaces after colonization by endothelial cells, at varying magnifications.
Figure 22B:
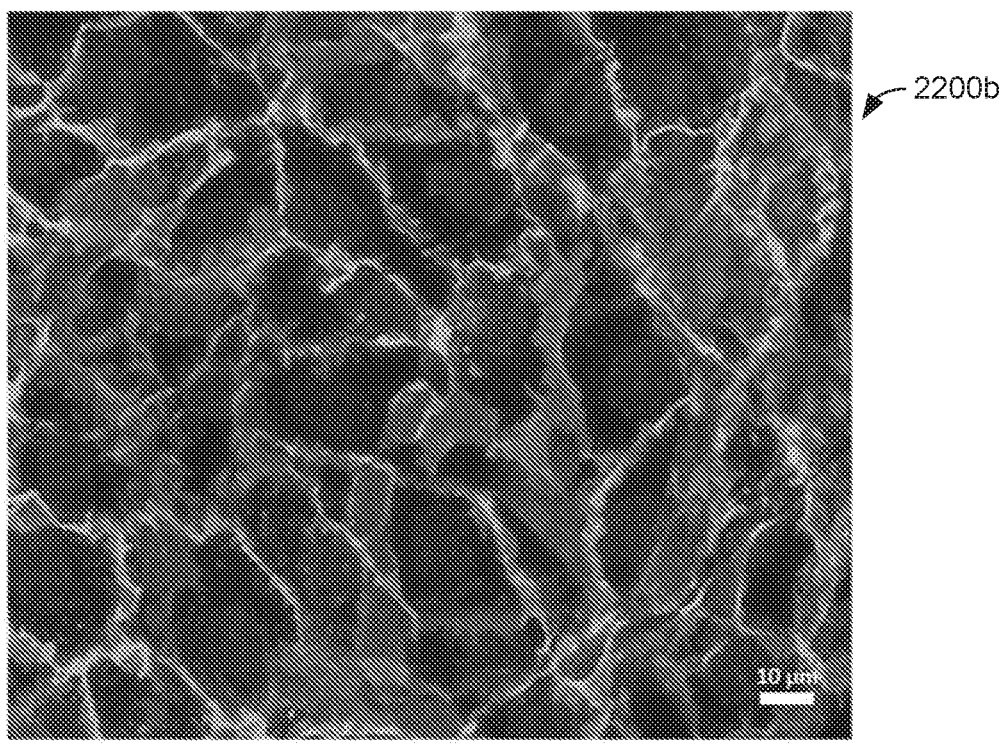

FIG. 22A and FIG. 22B are a pair of fluorescent microscope images of collagen-impregnated hydrogel surfaces after colonization by endothelial cells, at varying magnifications.

FIG. 22A is a first confocal micrograph 2200a of HUVECs seeded on the luminal surfaces of tubes composed of cross-linked, collagen I-treated F127-UDM hydrogel with collagen I additive, where cells stained with DAPI (blue: nuclei) and labelled via indirect immunofluorescence (green: CD31, interendothelial junction marker) exhibit characteristic cobblestone morphology. FIG. 22B is a second confocal micrograph 2200b under the same conditions as FIG. 22A, in higher magnification, to show additional detail.

Figure 23A:
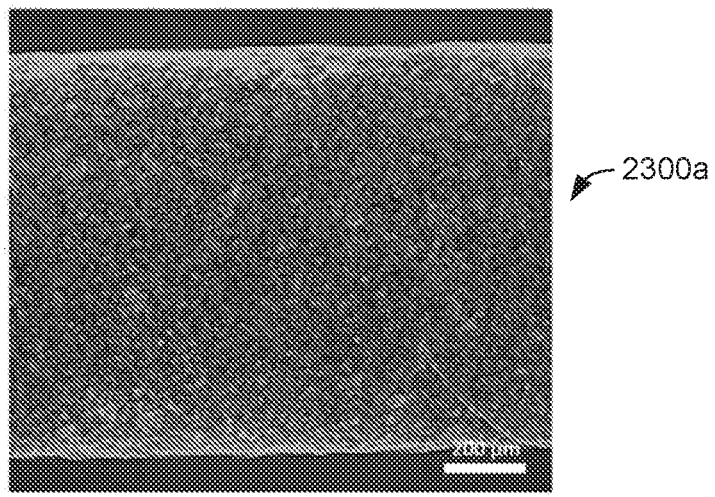
FIGS. 23A, 23B and 23C are a series of fluorescent microscope images of a collagen-impregnated hydrogel tube lumen section, after colonization by endothelial cells, in side-view, profile, and cross-section views.
Figure 23B:
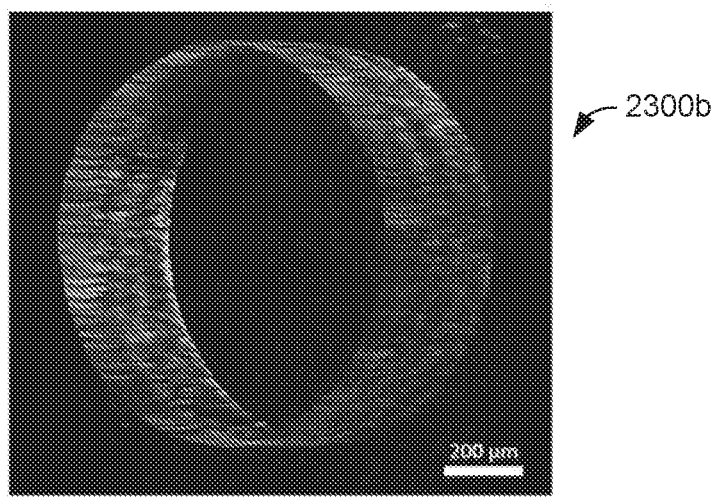
Figure 23C:
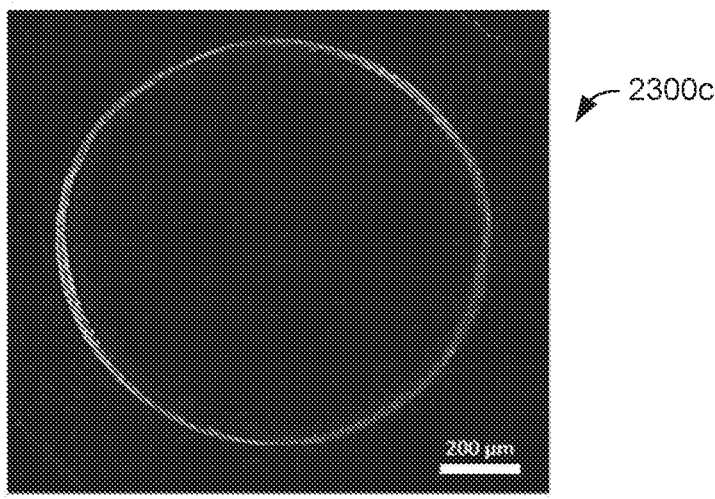

FIG. 23A, FIG. 23B, and FIG. 23C are a series of fluorescent microscope images of a collagen-impregnated hydrogel tube lumen sections, after colonization by endothelial cells, in side-view 2300a, profile 2300b, and cross-section 2300c views. In all three images, the luminal surface of the tube is visualized via confocal microscopy using identical cell staining to those used for FIGS. 22A and 22B, i.e., with the predominantly green field, indicative of an interendothelial junction marker, showing good cell coverage. Taken together, these results demonstrate that the coaxial extrusion platforms and hydrogel substrates (e.g. F127-UDM-based hydrogels) disclosed herein are effective in fabricating collagen-functionalized tubes, and these tubes are suitable for the culture of tubular monolayers of contiguous endothelial cells.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

As used herein and unless otherwise indicated, the terms "a" and "an" are taken to mean "one", "at least one" or "one or more". Unless otherwise required by context, singular terms used herein shall include pluralities and plural terms shall include the singular.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

All of the references cited herein are incorporated by reference. Aspects of the disclosure can be modified, if necessary, to employ the systems, functions, and concepts of the above references and application to provide yet further embodiments of the disclosure. These and other changes can be made to the disclosure in light of the detailed description.

Specific elements of any foregoing embodiments can be combined or substituted for elements in other embodiments. Moreover, the inclusion of specific elements in at least some of these embodiments may be optional, wherein further embodiments may include one or more embodiments that specifically exclude one or more of these specific elements. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

In the following, further examples are described to facilitate the understanding of the invention:

Example A. A method of preparing a hydrogel tube, the method comprising: with a nozzle assembly having an annular outer nozzle; extruding a first cross-linkable hydrogel solution via the annular outer nozzle to form an outer cross-linkable hydrogel tube; and curing the outer cross-linkable hydrogel tube to form a cross-linked hydrogel tube.

Example B. The method of example A, wherein:
the nozzle assembly comprises a bell nozzle; and
extruding the first cross-linkable hydrogel solution comprises extruding a hollow cylindrical sheet of the first cross-linkable hydrogel solution.

Example C. The method of example A, wherein:
the nozzle assembly further comprises an axial inner nozzle circumscribed by the annular outer nozzle; and
the method further comprises coextruding a second hydrogel solution via the axial inner nozzle while extruding the first cross-linkable hydrogel solution to form an inner hydrogel filament coaxially positioned within the cross-linkable hydrogel tube.

Example D. The method of example C, further comprising:
prior to coextruding the second hydrogel solution,
cooling the second hydrogel solution to cause the second hydrogel solution to transition from a gel state to a sol state;
loading the second hydrogel solution in the sol state into a second pneumatic syringe barrel; and
causing the second hydrogel solution in the second pneumatic syringe barrel to transition from the sol state to the gel state.

Example E. The method of example 3 or example 4, further comprising:
while coextruding the second hydrogel solution, increasing a wall thickness of the cross-linkable hydrogel tube by increasing a first pressure of extrusion of the first cross-linkable hydrogel solution from the annular outer nozzle.

Example F. The method of any one of example C through example E, further comprising:
while coextruding the second hydrogel solution, increasing a luminal dimeter of the cross-linkable tube by increasing a second pressure of extrusion of the second hydrogel solution from the axial inner nozzle.

Example G. The method of any one of example C through example F, wherein the inner hydrogel filament comprises a water-soluble hydrogel.

Example H. The method of any one of example C through example F, wherein the inner hydrogel filament comprises F127 hydrogel, poly(alkyl glycidyl ether)s hydrogels, or other shear-thinning hydrogel.

Example I. The method of any one of example C through example H, further comprising dissolving the inner hydrogel filament after curing the cross-linkable hydrogel tube.

Example J. The method of example I, further comprising filling the cross-linked hydrogel tube with a media solution containing live organisms after dissolving the inner hydrogel filament.

Example K. The method of example J, wherein the media solution comprises cross-linkable hydrogel, the method further comprising curing the cross-linkable hydrogel in the media solution to form a hydrogel matrix within the cross-linked hydrogel tube containing the live organisms.

Example L. The method of any one of example C through example K, further comprising:
injecting a first plug of cross-linkable hydrogel solution into a first open end of the cross-linked hydrogel tube;
curing the first plug of cross-linkable hydrogel solution to seal the first open end;
injecting a second plug of cross-linkable hydrogel solution into a second open end of the cross-linked hydrogel tube; and
curing the second plug of cross-linkable hydrogel solution to seal the second open end.

Example M. The method of any one of example C through example F, wherein:
the second hydrogel solution comprises a second cross-linkable UV-curable hydrogel; and
the method further comprises curing the inner hydrogel filament by exposing the inner hydrogel filament within the cross-linkable hydrogel tube to UV light after coextruding the second hydrogel solution.

Example N. The method of any one of the preceding examples, wherein the first cross-linkable hydrogel solution comprises a shear-thinning hydrogel.

Example O. The method of any one of the preceding examples, wherein:
the cross-linkable hydrogel tube is UV-curable; and
curing the cross-linkable hydrogel tube comprises exposing the cross-linkable hydrogel tube to UV light.

Example P. The method of any one of the preceding examples, wherein the cross-linkable hydrogel tube comprises at least one of F-127-DMA, F127-UDM, F127-UUDM, or F127-UDA polymers.

Example Q. The method of any one of the preceding examples, wherein the first cross-linkable hydrogel solution comprises at least one of F-127-DMA, F127-UDM, F127-UUDM, or F127-UDA polymers dissolved in an aqueous solution at a concentration of 20-35% weight percent.

Example R. The method of any one of the preceding examples, further comprising:
prior to extruding the first cross-linkable hydrogel solution,
cooling the first cross-linkable hydrogel solution to 1-20 degrees;
loading the cooled first cross-linkable hydrogel solution into a first pneumatic syringe barrel fluidly connected with the annular outer nozzle; and
warming the first cross-linkable hydrogel solution to between 18-50 degrees.

Example S. The method of any one of the preceding examples, wherein:
the first cross-linkable hydrogel solution comprises a first collagen suspension and
an inner lumen of the cross-linked hydrogel tube comprises a collagen-impregnated hydrogel surface.

Example T. The method of example S, further comprising:
dehydrating the cross-linked hydrogel tube after the curing of the cross-linkable hydrogel tube; and
rehydrating the cross-linked hydrogel tube with a second collagen suspension to bind additional collagen to the collagen-impregnated hydrogel surface on the inner lumen of the cross-linked hydrogel tube.

Example U. The method of example S or example T, further comprising seeding live cells on the collagen-impregnated hydrogel surface.

Example V. The method of any one of example S through example U, further comprising seeding live human endothelial cells on the collagen-impregnated hydrogel surface.

Example W. A hydrogel tube prepared according to the method of any one of the preceding examples.

Example X. The hydrogel tube of example W, wherein the hydrogel tube has a luminal diameter of less than 0.5 mm, preferably less than or equal to 0.43 mm, and more preferably less than or equal to 0.20 mm.

Example Y. The hydrogel tube of example W or example X, wherein the hydrogel tube has an outer diameter of less than 5 mm, preferably less than or equal to 1 mm.

Example Z. The hydrogel tube of any one of example V through example Y, wherein the hydrogel tube has an outer wall thickness of less than 1 mm, preferably less than or equal to 0.5 mm.

Example AA. A method of fabricating a hydrogel tube, the method comprising:
cooling a first hydrogel solution to a first temperature of less than or equal to 20 degrees Celsius, preferably less than or equal to 6 degrees Celsius;
loading the first hydrogel solution into a first pneumatic syringe barrel;
cooling a second hydrogel solution to a second temperature of less than or equal to 20 degrees Celsius, preferably less than or equal to 6 degrees Celsius;
loading the second hydrogel solution into a second pneumatic syringe barrel;
warming the first hydrogel solution within the first pneumatic syringe barrel to a third temperature that is greater than the first temperature;
warming the second hydrogel solution within the second pneumatic syringe barrel to a fourth temperature that is greater than the second temperature;
attaching the first pneumatic syringe barrel to a first inlet of a concentric nozzle assembly, the first inlet being fluidly connected with an annular nozzle outlet of the concentric nozzle assembly;
attaching the second pneumatic syringe barrel to a second inlet of the concentric nozzle assembly, the second inlet being fluidly connected with an axial nozzle outlet of the concentric nozzle assembly that is circumscribed by the annular nozzle outlet;
coextruding the first hydrogel solution from the annular nozzle outlet and the second hydrogel solution from the axial nozzle outlet to form a coaxial hydrogel filament comprising a cross-linkable hydrogel tube surrounding an inner support hydrogel filament;
curing the cross-linkable hydrogel tube to form a durable hydrogel tube; and
removing the inner support hydrogel filament from the durable hydrogel tube.

Example AB. The method of example AA wherein the first hydrogel solution comprises at least one of F-127-DMA, F127-UDM, F127-UUDM, or F127-UDA polymers dissolved in an aqueous solution at a concentration of 20-35% weight percent.

Example AC. The method of example AA or example AB, wherein curing the cross-linkable hydrogel tube comprises photo-curing the cross-linkable hydrogel tube by exposure to UV light.

Example AD. The method of any one of examples AA to AC, wherein:
the first hydrogel solution is capable of gel-to-sol transition while cooling from room temperature to 5-15 degrees Celsius; and
the method further comprises homogenously incorporating one or more of monomers, polymers, biopolymers, nanopolymers, or living cells within the first hydrogel solution.

Example AE. The method of any one of example AA through example AD, wherein the first hydrogel solution is capable of shear-thinning during extrusion.

Example AF. The method of any one of examples AA through example AE, wherein coextruding the first hydrogel solution and the second hydrogel solution comprises simultaneously extruding the first hydrogel solution at a first rate and extruding the second hydrogel solution at a second rate different from the first rate.

Example AG. The method of any one of example AA through example AF, further comprising seeding endothelial cells on a luminal surface of the durable hydrogel tube.

Example AH. The method of example AG, further comprising:
prior to the coextrusion of the first hydrogel solution from the annular nozzle outlet and the second hydrogel solution from the axial nozzle outlet, impregnating the first hydrogel solution with collagen;
dehydrating the durable hydrogel tube; and rehydrating the durable hydrogel tube with a collagen suspension.

Example AI. A hydrogel tube fabricated according to any one of example AA through example AH.

Example AJ. A method of fabricating a hydrogel tube, the method comprising:
  extruding a first cross-linkable hydrogel solution to form a cross-linkable hydrogel tube;
  curing the cross-linkable hydrogel tube to form a durable hydrogel tube; and
  seeding endothelial cells on a luminal surface of the durable hydrogel tube.

Example AK. The method of example AJ, wherein the first cross-linkable hydrogel solution comprises a collagen additive.

Example AL. The method of example AK, further comprising, prior to culturing the endothelial cells, at least partially dehydrating the durable hydrogel tube and rehydrating the durable hydrogel tube with a collagen solution.

Example AM. The method of any one of examples AJ-AL, wherein:
  the extrusion of the first cross-linkable hydrogel solution to form the cross-linkable hydrogel tube comprises coextruding the first cross-linkable hydrogel solution from an outer nozzle of a nozzle assembly and a second hydrogel solution from an inner nozzle of the nozzle assembly to form a coaxial hydrogel filament comprising the cross-linkable hydrogel tube enclosing an inner hydrogel support filament; and
  the method further comprises removing the inner hydrogel support filament from the durable hydrogel tube.

Example AN. The method of any one of example AJ through example AL, further comprising culturing the endothelial cells to yield a tubular endothelial layer on the luminal surface.

Example AO. A hydrogel construct comprising the hydrogel tube prepared according to any one of example AJ through example AN.

Example AP. A hydrogel construct, comprising:
  a cured hydrogel tube comprising a cross-linked hydrogel tube defining a luminal surface comprising collagen; and
  endothelial cells seeded on the luminal surface of the cured hydrogel tube.

Example AQ. The hydrogel construct of example AP, wherein the endothelial cells comprise a tubular endothelial layer on the luminal surface of the cured hydrogel tube.

Example AR. The hydrogel construct of example AP or example AQ, wherein the cured hydrogel tube has a luminal diameter of less than 0.5 mm, preferably less than or equal to 0.43 mm, and more preferably less than or equal to 0.20 mm.

Example AS. The hydrogel construct of any one of example AP through example AR, further comprising a hydrogel support filament contained in a lumen of the cured hydrogel tube.

Example AT. The hydrogel construct of any of one example AP through example AR, further comprising a media solution containing live organisms within a lumen of the cured hydrogel tube.

Example AU. The hydrogel construct of any of one example AP through example AR, further comprising a hydrogel matrix containing live organisms within a lumen of the cured hydrogel tube.

Example AV. The hydrogel construct of any of one example AP through example AU, wherein the cross-linked hydrogel tube comprises at least one of F-127-DMA, F127-UDM, F127-UUDM, or F127-UDA polymers.

Example AW. The hydrogel construct of any of one example AP through example AV, wherein the cured hydrogel tube has an outer diameter of less than 1 mm, preferably less than or equal to 0.5 mm.

Example AX. A hydrogel construct, comprising:
  a cured hydrogel tube comprising a cross-linked hydrogel; and
  a media solution containing live organisms within a lumen of the cured hydrogel tube.

Example AY. The hydrogel construct of example AX, wherein the cured hydrogel tube has a luminal diameter of less than 0.5 mm, preferably less than or equal to 0.43 mm, and more preferably less than or equal to 0.20 mm.

Example AZ. The hydrogel construct of any of one example AX and example AY, wherein the media solution comprises a hydrogel matrix.

Example BA. The hydrogel construct of any one of example AX through example AZ, wherein:
  the cured hydrogel tube is sealed by cured hydrogel; and
  the live organisms are capable of producing bioproducts capable of permeating through the cured hydrogel tube.

Example BB. The hydrogel construct of any one of example AX through example BA, wherein the live organisms comprise yeast cells.

Example BC. The hydrogel construct of example BB, wherein the cured hydrogel tube is permeable to fermentation reagents and products.

Example BD. The hydrogel construct of example AX, wherein the media solution containing live organisms comprises a cured hydrogel filament positioned within the cured hydrogel tube, the cured hydrogel filament comprising yeast cells embedded within cross-linked hydrogel.

Example BE. A system for fabricating a hydrogel tube, the system comprising:
  a nozzle assembly, comprising:
  a nozzle body;
  a first fluid inlet in the nozzle body;
  a first source of cross-linkable hydrogel solution fluidly connected with the nozzle body at the first fluid inlet;
  a second fluid inlet in the nozzle body separate from the first fluid inlet;
  a second source of hydrogel solution, different from the source of cross-linkable hydrogel solution, fluidly connected with the nozzle body at the second fluid inlet;
  an inner nozzle outlet at an apical end of the nozzle body fluidly connected with the second fluid inlet and aligned with an axis of extrusion; and
  an outer nozzle outlet at the apical end of the nozzle body fluidly connected with the first fluid inlet and circumscribing the inner nozzle outlet, the outer nozzle outlet angled toward the axis of extrusion such that, in use, fluid extruded from the outer nozzle outlet would contact fluid extruded from the inner nozzle outlet;
  a first injection assembly operable to inject a first cross-linkable hydrogel solution into the first fluid inlet from the first source; and
  a second injection assembly operable to inject a second hydrogel solution into the second fluid inlet from the second source.

Example BF. The system of example BE, wherein the outer nozzle outlet is annular.

Example BG. The system of any one of example BE or example BF, wherein:
  the first injection assembly comprises a first pneumatic syringe adapter connected to the first fluid inlet; and the second injection assembly comprises a second pneumatic syringe adapter connected to the second fluid inlet.

Example BH. The system of any one of example BE through example BG, wherein:
the first fluid inlet is positioned in-line with the axis of extrusion and opposite the apical end of the nozzle body; and
the second fluid inlet is positioned laterally with respect to the axis of extrusion along a sidewall of the nozzle body.

Example BI. A hydrogel tube, comprising a cross-linked hydrogel comprising at least one of F-127-DMA, F127-UDM, F127-UUDM, or F127-UDA polymer, the hydrogel tube having a length of at least 12 5 cm, preferably at least 15 cm, and a luminal diameter less than or equal to 0.5 cm, preferably less than or equal to 0.1 mm.

What is claimed is:

1. A method of fabricating a hydrogel tube, the method comprising:
extruding a hollow cylindrical sheet of a first cross-linkable hydrogel solution from a bell nozzle of a nozzle assembly at room temperature to form a cross-linkable hydrogel tube; and
curing the cross-linkable hydrogel tube to form a cross-linked hydrogel tube, wherein curing the cross-linkable hydrogel tube comprises photo-curing the cross-linkable hydrogel tube by exposure to UV light.

2. The method of claim 1, wherein:
the nozzle assembly further comprises an axial inner nozzle circumscribed by the bell nozzle; and
the method further comprises coextruding a second hydrogel solution via the axial inner nozzle while extruding the first cross-linkable hydrogel solution to form an inner hydrogel filament coaxially positioned within the cross-linkable hydrogel tube.

3. The method of claim 2, further comprising:
prior to coextruding the second hydrogel solution,
cooling the second hydrogel solution to cause the second hydrogel solution to transition from a gel state to a sol state;
loading the second hydrogel solution in the sol state into a second pneumatic syringe barrel; and
causing the second hydrogel solution in the second pneumatic syringe barrel to transition from the sol state to the gel state.

4. The method of claim 2, further comprising:
while coextruding the second hydrogel solution, increasing a wall thickness of the cross-linkable hydrogel tube by increasing a first pressure of extrusion of the first cross-linkable hydrogel solution from the bell nozzle.

5. The method of claim 2, further comprising:
while coextruding the second hydrogel solution, increasing a luminal diameter of the cross-linkable hydrogel tube by increasing a second pressure of extrusion of the second hydrogel solution from the axial inner nozzle.

6. The method of claim 2, wherein the inner hydrogel filament comprises poloxamer 407, poly(alkyl glycidyl ether)s hydrogels, or other shear-thinning hydrogel, or other shear-thinning and cross-linkable hydrogel.

7. The method of claim 1, further comprising:
prior to extruding the first cross-linkable hydrogel solution,
cooling the first cross-linkable hydrogel solution to 1-20 degrees Celsius;
loading the cooled first cross-linkable hydrogel solution into a first pneumatic syringe barrel fluidly connected with the bell nozzle; and
warming the first cross-linkable hydrogel solution to between 18-50 degrees Celsius.

8. A method of fabricating a hydrogel tube, the method comprising:
cooling a first hydrogel solution to a first temperature of less than or equal to 20 degrees Celsius;
loading the first hydrogel solution into a first pneumatic syringe barrel;
cooling a second hydrogel solution to a second temperature of less than or equal to 20 degrees Celsius;
loading the second hydrogel solution into a second pneumatic syringe barrel;
warming the first hydrogel solution within the first pneumatic syringe barrel to a third temperature that is greater than the first temperature;
warming the second hydrogel solution within the second pneumatic syringe barrel to a fourth temperature that is greater than the second temperature;
attaching the first pneumatic syringe barrel to a first inlet of a concentric nozzle assembly, the first inlet being fluidly connected with an annular nozzle outlet of the concentric nozzle assembly;
attaching the second pneumatic syringe barrel to a second inlet of the concentric nozzle assembly, the second inlet being fluidly connected with an axial nozzle outlet of the concentric nozzle assembly that is circumscribed by the annular nozzle outlet;
coextruding the first hydrogel solution from the annular nozzle outlet and the second hydrogel solution from the axial nozzle outlet to form a coaxial hydrogel filament comprising a cross-linkable hydrogel tube surrounding an inner support hydrogel filament;
curing the cross-linkable hydrogel tube to form a durable hydrogel tube, wherein curing the cross-linkable hydrogel tube comprises photo-curing the cross-linkable hydrogel tube by exposure to UV light; and
removing the inner support hydrogel filament from the durable hydrogel tube.

9. The method of claim 8 wherein the first hydrogel solution comprises at least one of poloxamer 407-DMA, poloxamer 407-UDM, poloxamer 407-UUDM, or poloxamer 407-UDA polymers dissolved in an aqueous solution at a concentration of 20-35% weight percent.

10. The method of claim 8 wherein the first temperature is less than or equal to 6 degrees Celsius.

11. The method of claim 8 wherein the second temperature is less than or equal to 6 degrees Celsius.

12. The method of claim 8, wherein the inner support hydrogel filament comprises poloxamer 407, poly(alkyl glycidyl ether)s hydrogels, or other shear-thinning hydrogel, or other shear-thinning and cross-linkable hydrogel.

* * * * *